United States Patent [19]
Kordis et al.

[11] Patent Number: 5,928,228
[45] Date of Patent: *Jul. 27, 1999

[54] FLEXIBLE HIGH DENSITY MULTIPLE ELECTRODE CIRCUIT ASSEMBLIES EMPLOYING RIBBON CABLE

[75] Inventors: Thomas F. Kordis; Dorin Panescu, both of Sunnyvale; David K. Swanson, Mountain View, all of Calif.

[73] Assignee: EP Technologies, Inc., Sunnyvale, Calif.

[*] Notice: This patent is subject to a terminal disclaimer.

[21] Appl. No.: 08/801,483

[22] Filed: Feb. 18, 1997

Related U.S. Application Data

[63] Continuation of application No. 08/466,234, Jun. 6, 1995, abandoned, which is a continuation of application No. 08/206,413, Mar. 4, 1994, abandoned, which is a continuation-in-part of application No. 08/033,640, Mar. 16, 1993, abandoned.

[51] Int. Cl.$^6$ ................................................. A61B 17/39
[52] U.S. Cl. ........................... 606/41; 607/122; 600/374
[58] Field of Search ........................... 606/41, 42, 45–50; 607/100–102, 122; 600/372–374, 393; 29/855, 877, 825; 156/47, 51, 55

[56] References Cited

U.S. PATENT DOCUMENTS

| | | |
|---|---|---|
| 3,557,794 | 1/1971 | Van Patten . |
| 4,461,304 | 7/1984 | Kuperstein ............................. 128/642 |
| 5,010,894 | 4/1991 | Edhag . |
| 5,156,151 | 10/1992 | Imran ..................................... 128/642 |
| 5,201,903 | 4/1993 | Corbett, III et al. ..................... 607/57 |
| 5,255,679 | 10/1993 | Imran ..................................... 128/642 |
| 5,293,869 | 3/1994 | Edwards et al. ........................ 128/642 |
| 5,343,860 | 9/1994 | Metzger et al. ......................... 128/642 |
| 5,515,848 | 5/1996 | Corbett, III et al. .................... 600/374 |
| 5,524,338 | 6/1996 | Martyniuk et al. ....................... 29/825 |

Primary Examiner—Michael Peffley
Attorney, Agent, or Firm—Lyon & Lyon LLP

[57] ABSTRACT

An electrode circuit has a distal region for carrying at least one electrode, a proximal region for connection to external apparatus, and an intermediate region electrically coupling the distal region with the proximal region. At least one, and preferably all, of the regions comprises flexible ribbon cable having two or more adjacent tracks of electrical conduction material and adjoining electrical insulating material. Use of ribbon cable make possible highly dense, extremely reliable electrical connections. Its reliability and density obviate the need for complicated multiplexing schemes at the distal region. Instead, less complicated, proximal multiplexing schemes can be used.

51 Claims, 23 Drawing Sheets

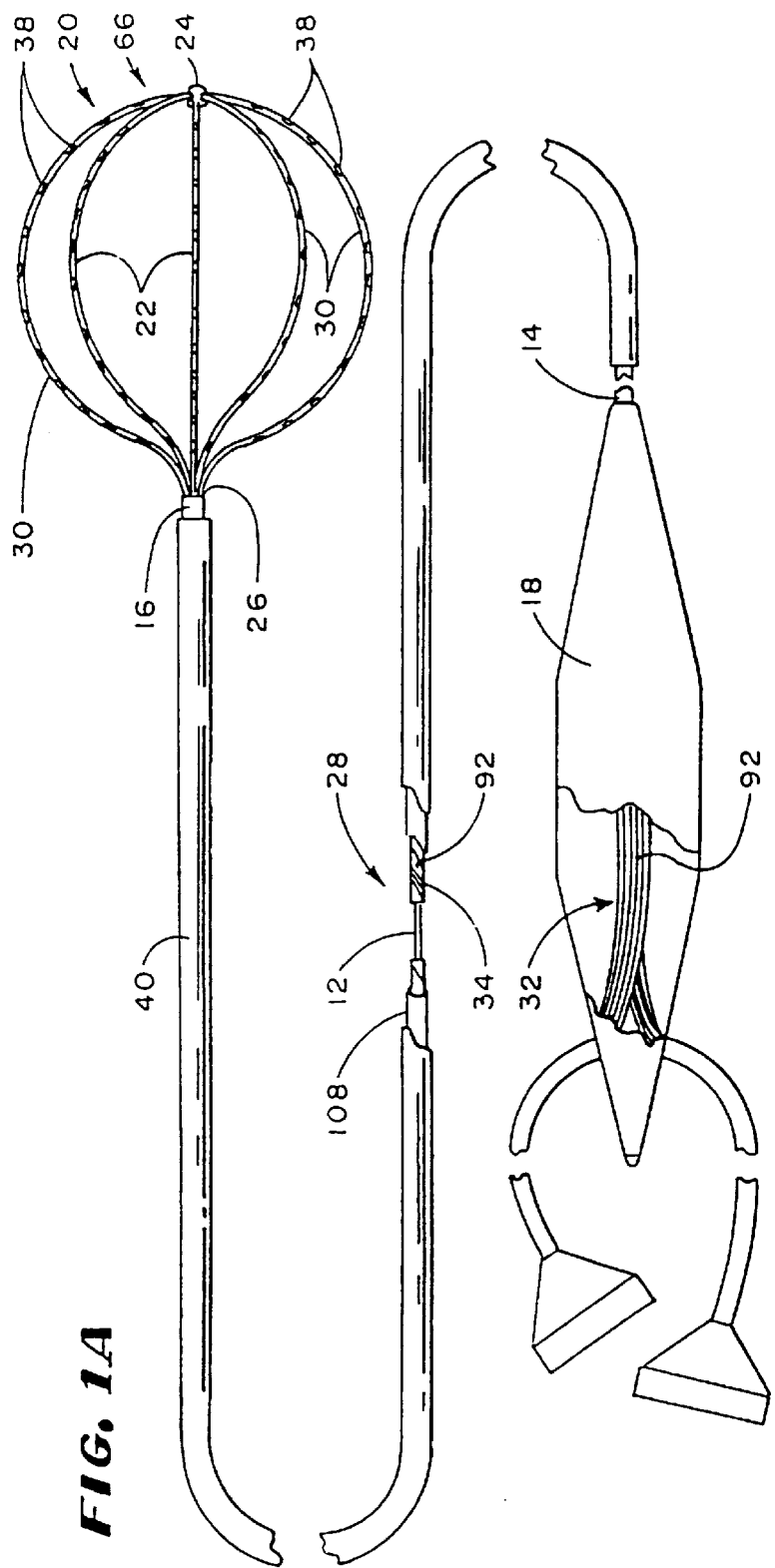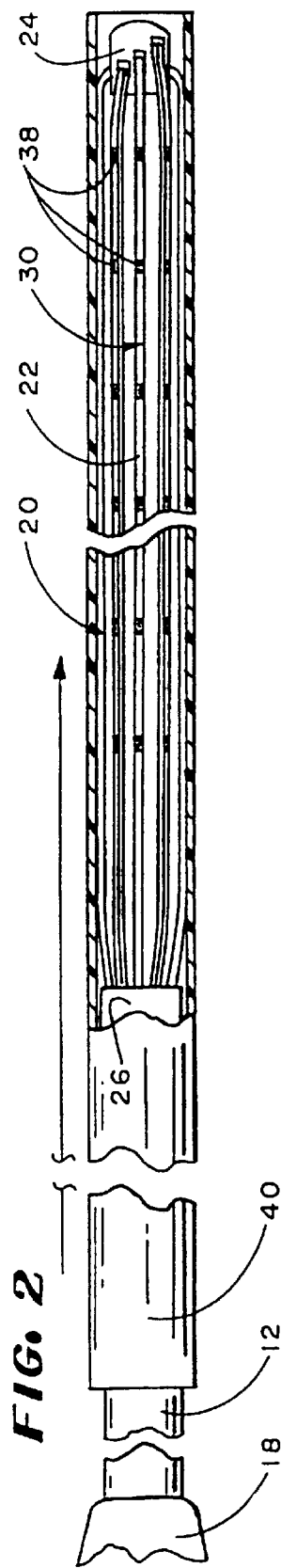

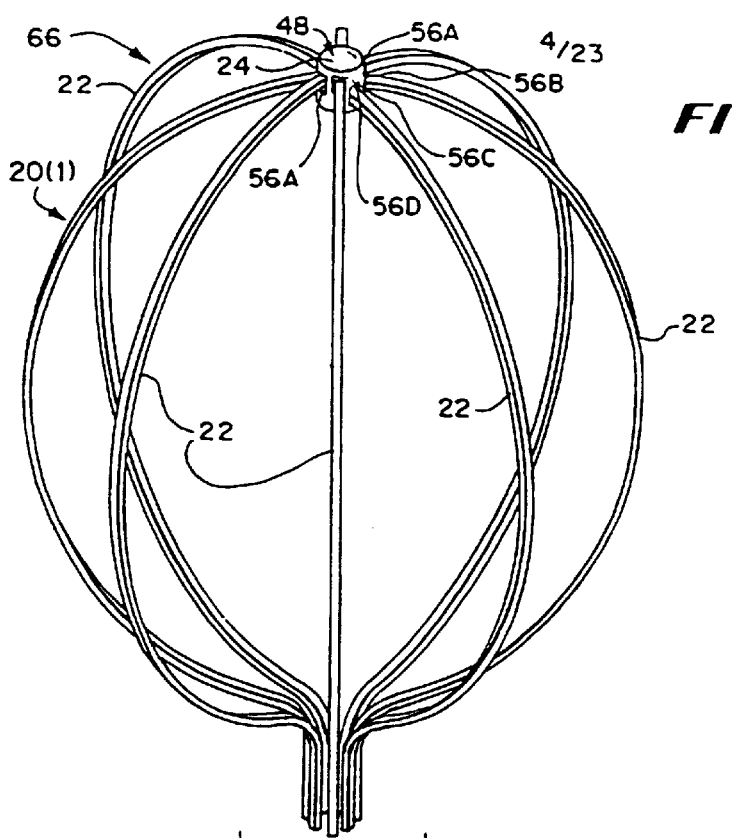
FIG. 10
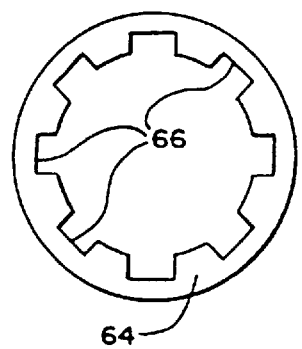
FIG. 11
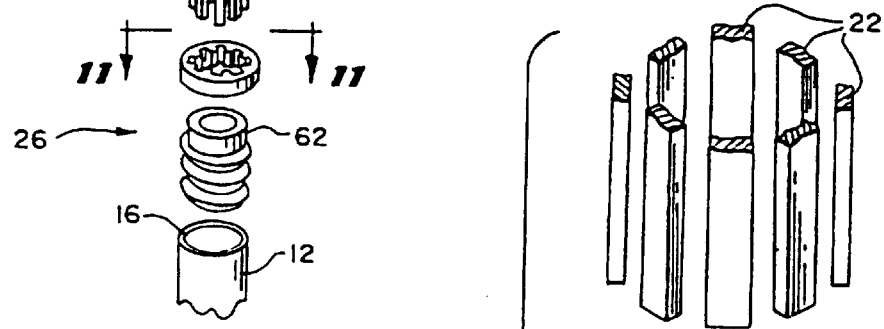
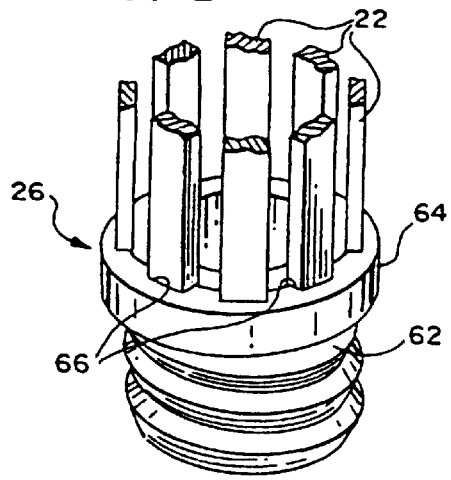
FIG. 13
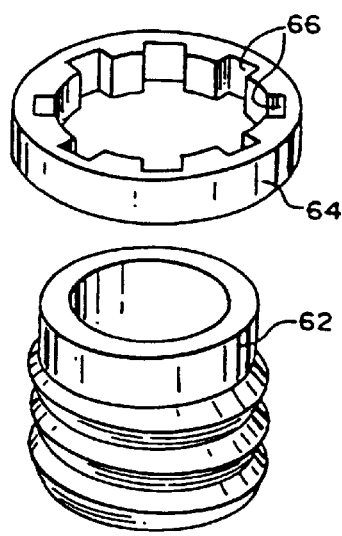
FIG. 12

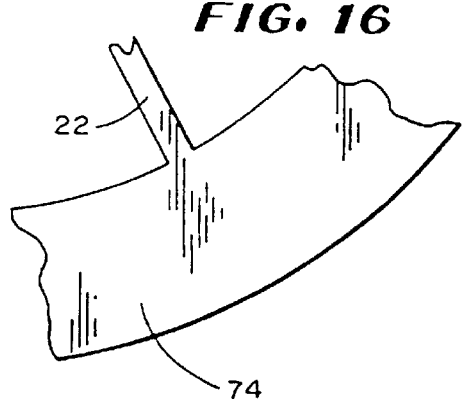
FIG. 16
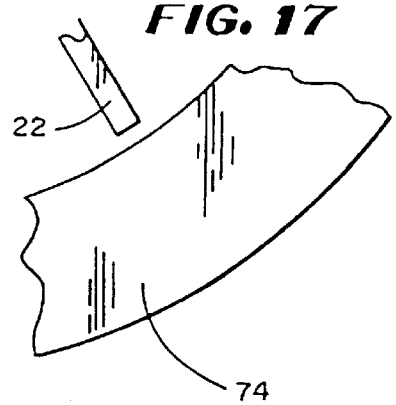
FIG. 17
FIG. 18
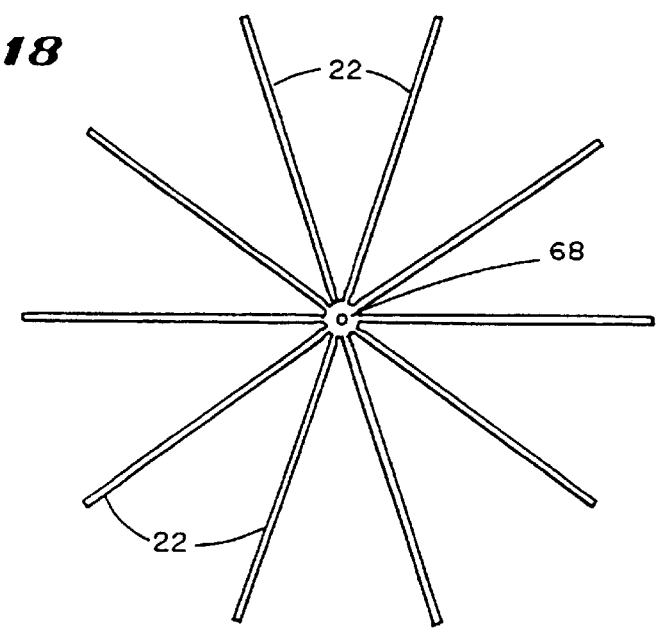
FIG. 19
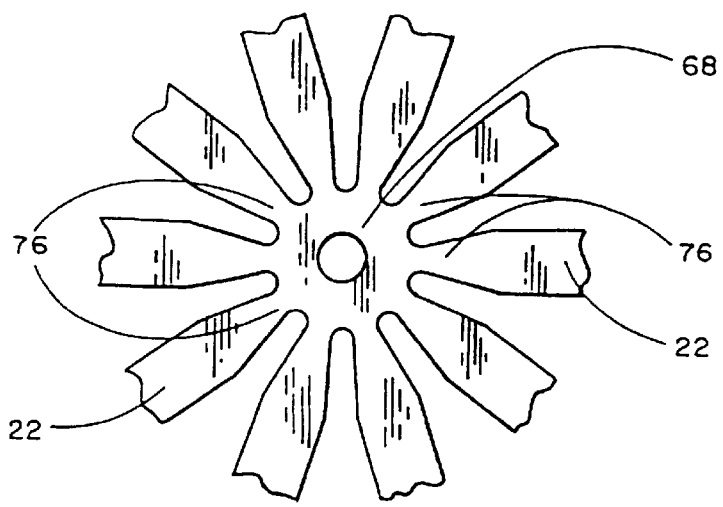

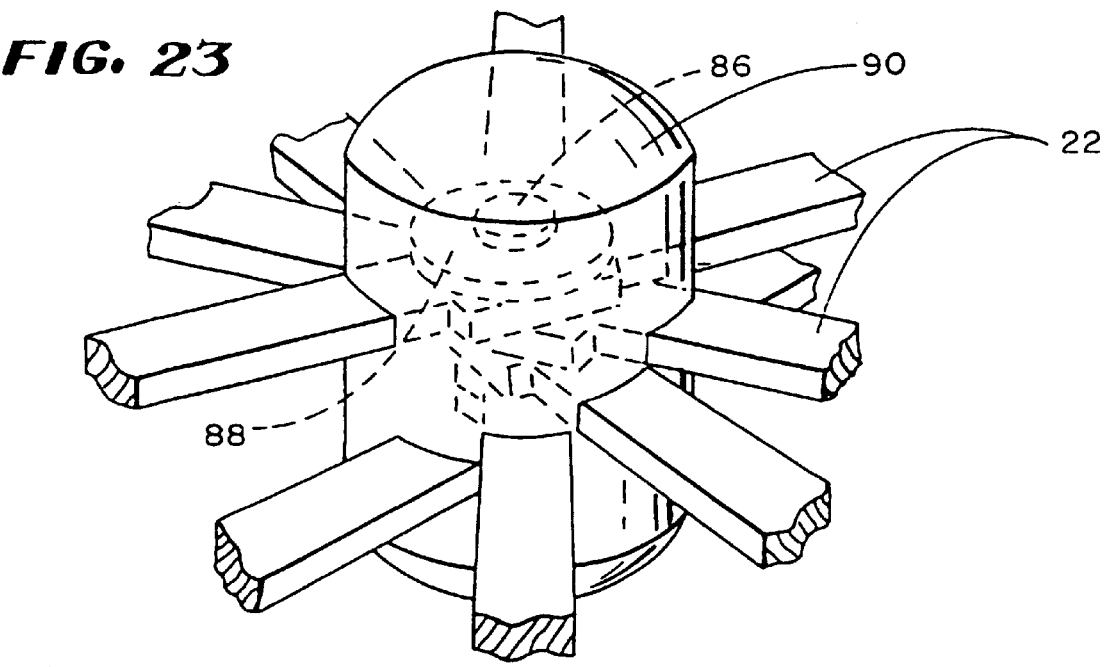
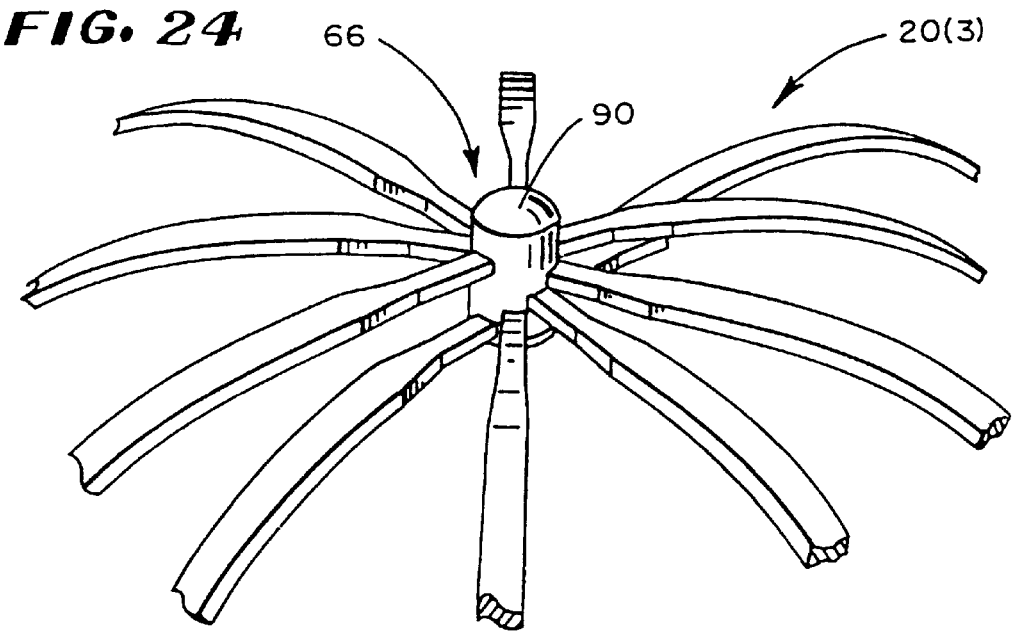

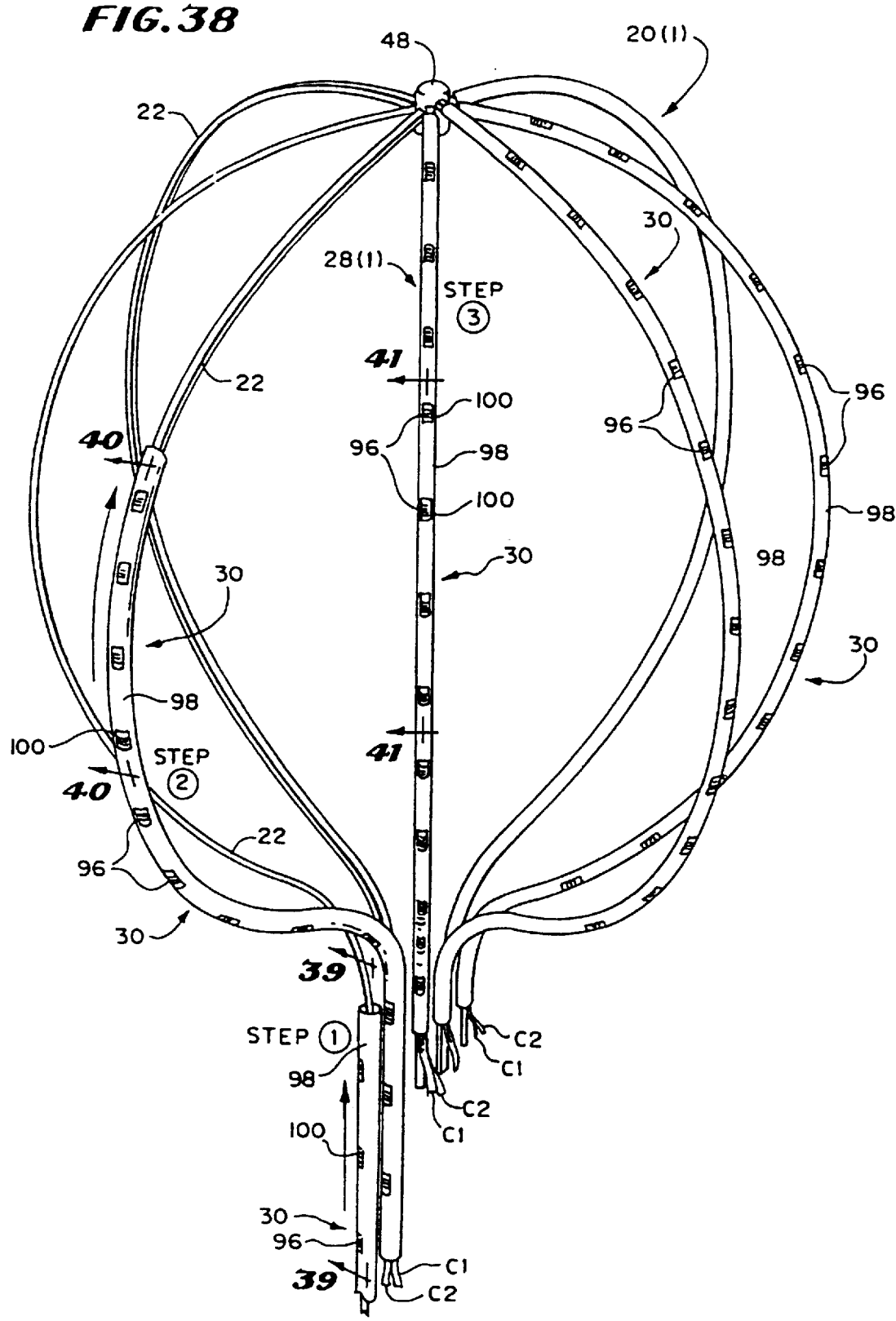

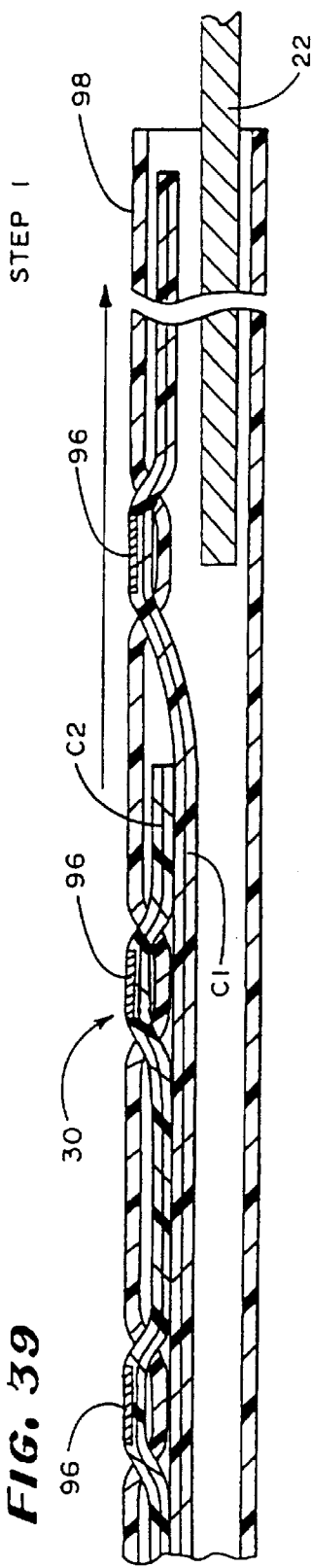
FIG. 39 STEP 1
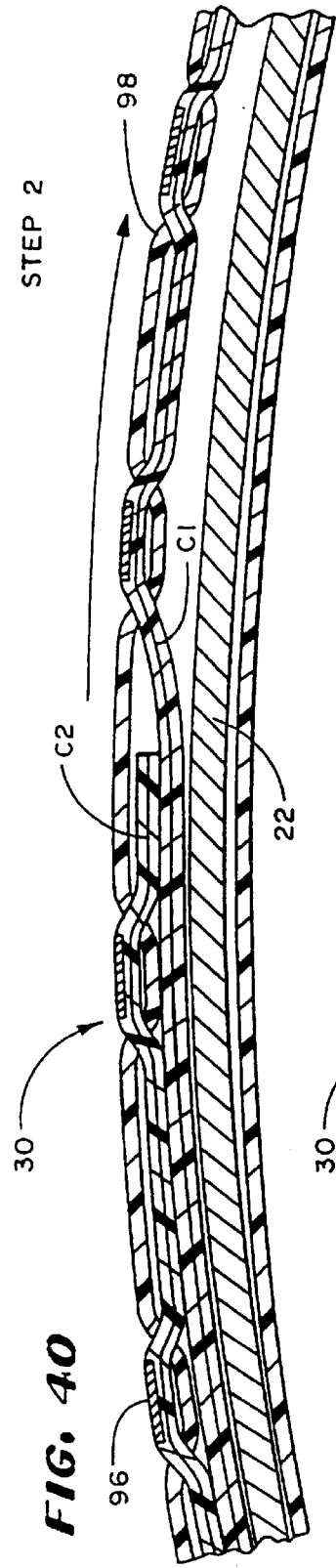
FIG. 40 STEP 2
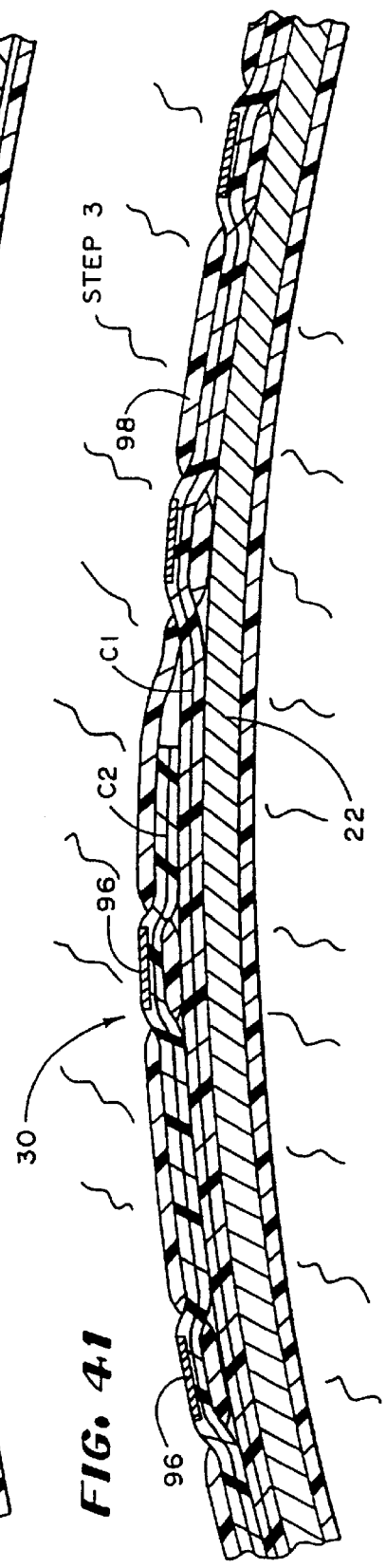
FIG. 41 STEP 3

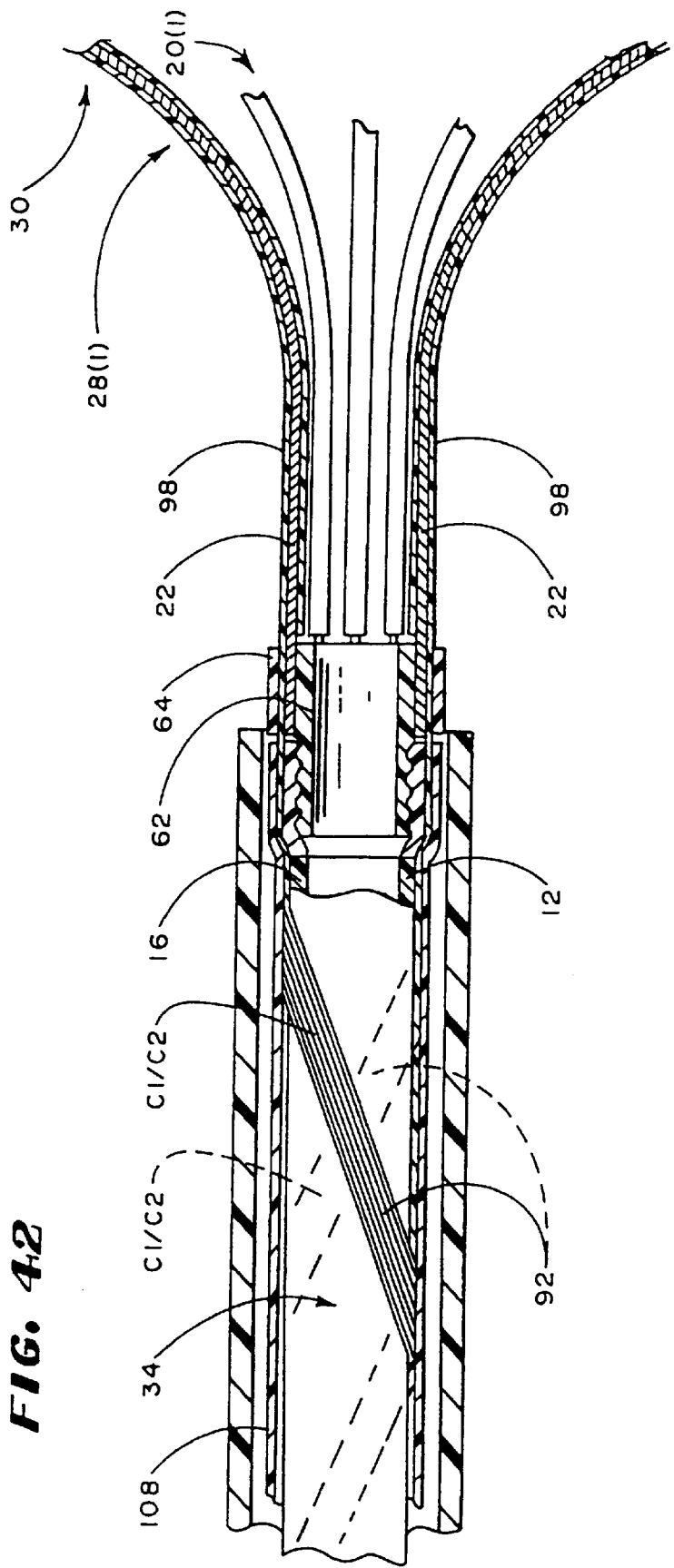

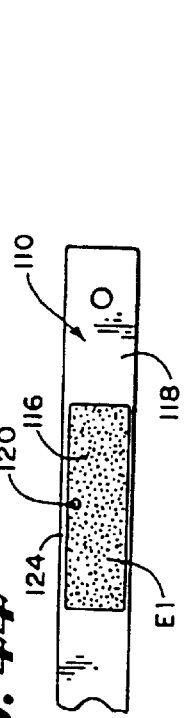
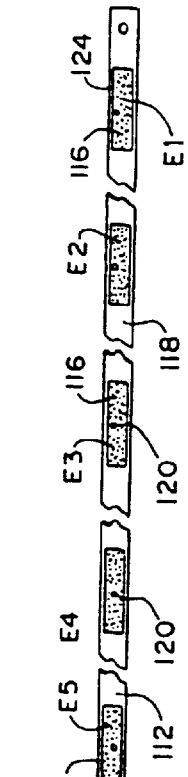
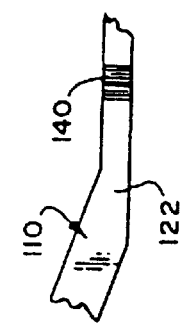
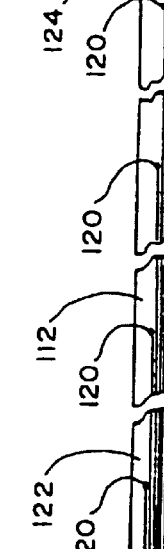
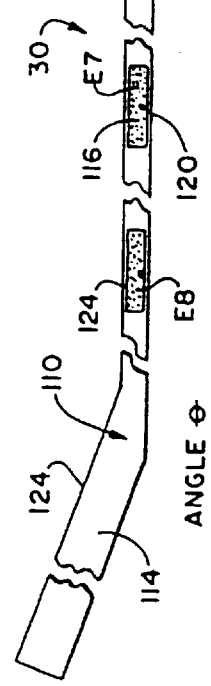
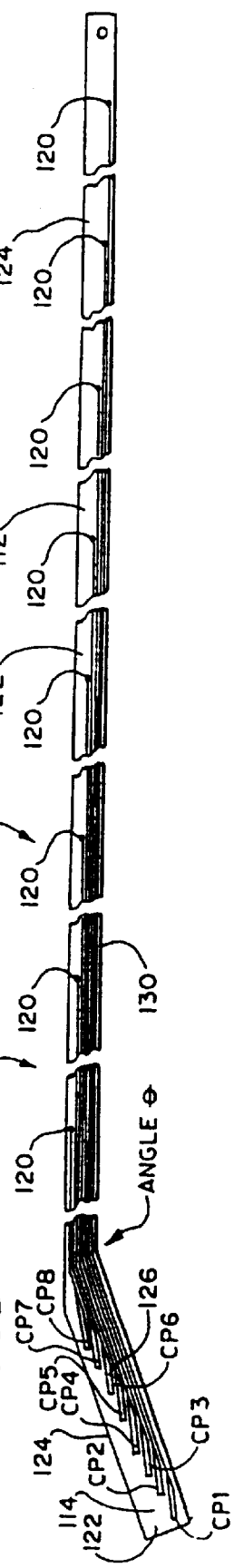
FIG. 44
FIG. 46
FIG. 43
FIG. 45

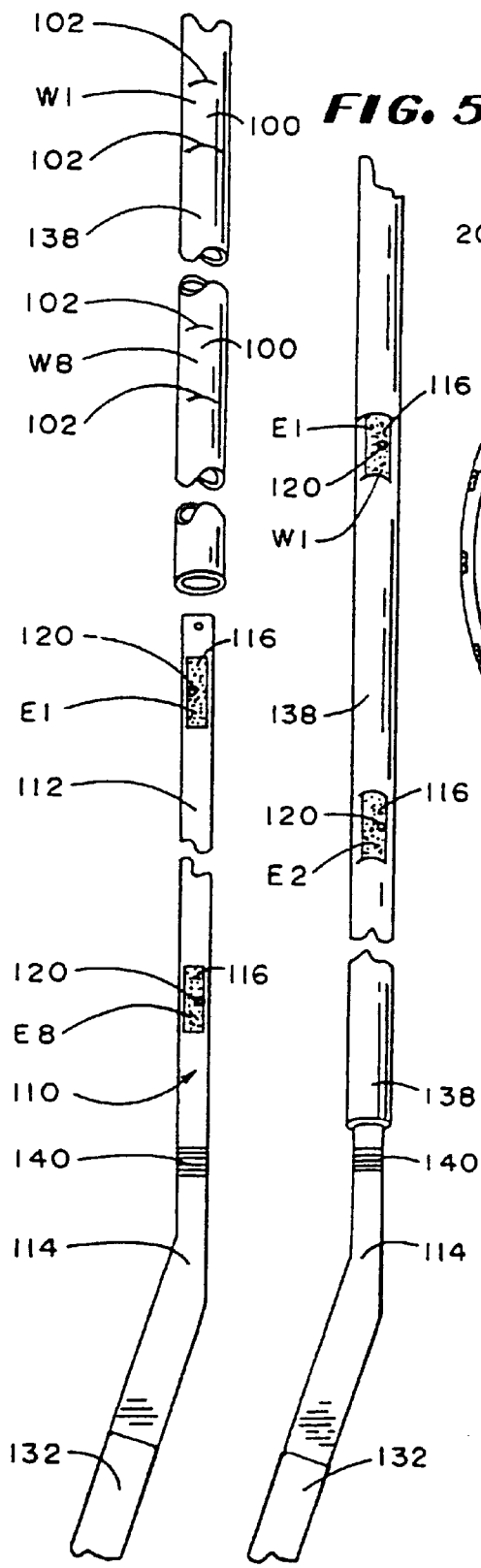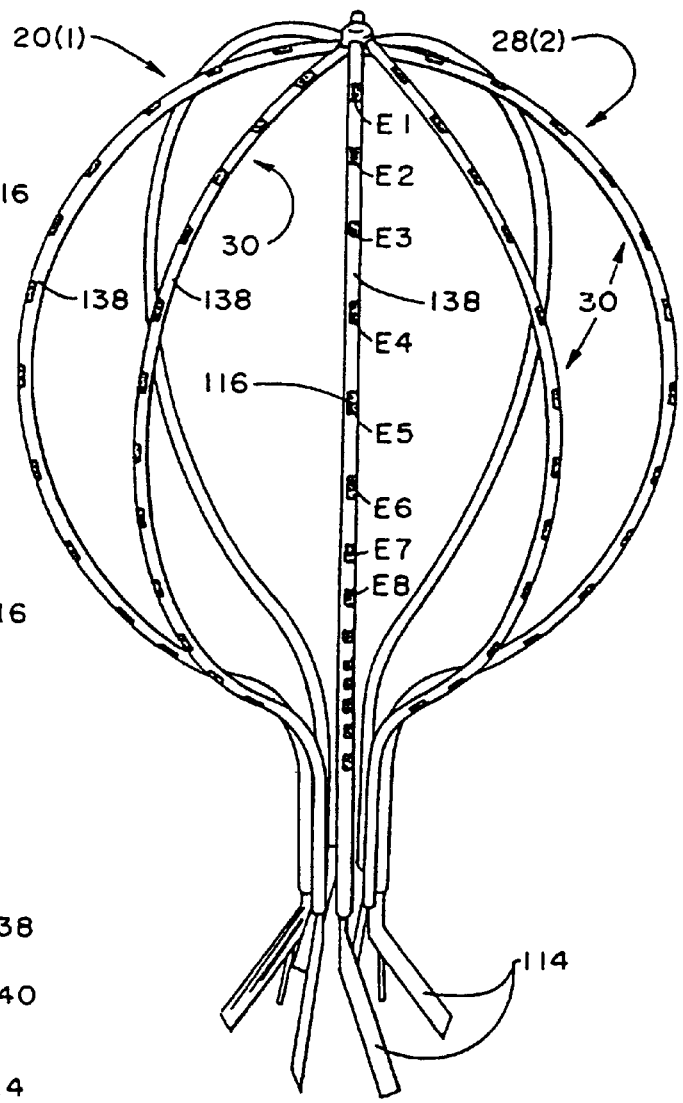

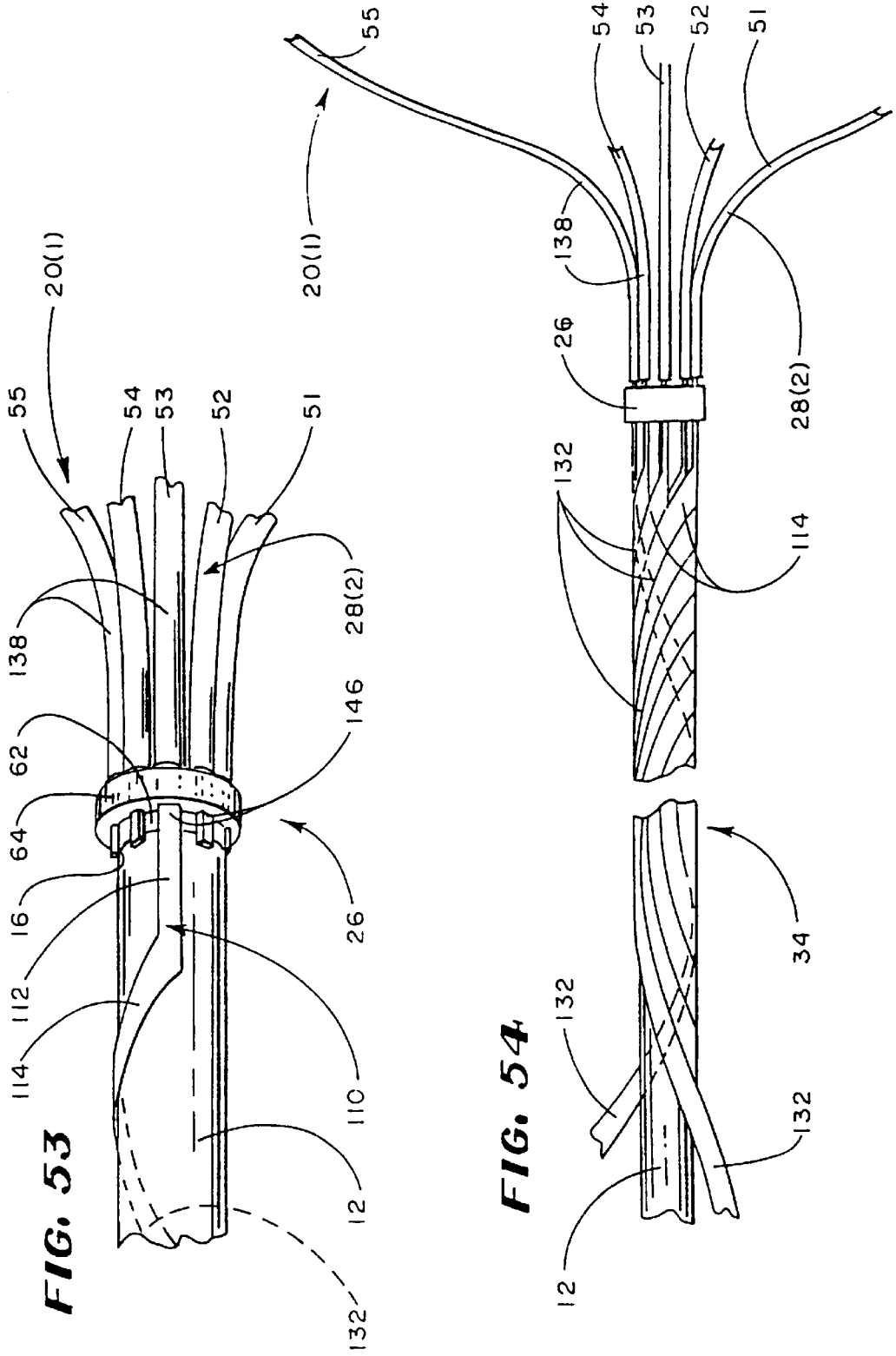

FLEXIBLE HIGH DENSITY MULTIPLE ELECTRODE CIRCUIT ASSEMBLIES EMPLOYING RIBBON CABLE

This is a continuation of Ser. No. 08/466,234 filed Jun. 6, 1995(now abandoned); which is a continuation of Ser. No. 08/206,413 filed on Mar. 4, 1994(now abandoned); which is a continuation-in-part of application Ser. No. 08/033,640, filed Mar. 16, 1993(abandoned).

FIELD OF THE INVENTION

The invention relates to systems and methods for mapping and ablating the interior regions of the heart for treatment of cardiac conditions.

BACKGROUND OF THE INVENTION

Physicians make use of catheters today in medical procedures to gain access into interior regions of the body to ablate targeted tissue areas. It is important for the physician to be able to precisely locate the catheter and control its emission of energy within the body during tissue ablation procedures.

The need for precise control over the catheter is especially critical during procedures that ablate endocardial tissue within the heart. These procedures, called electrophysiological therapy, are use to treat cardiac rhythm disturbances.

During these procedures, a physician steers a catheter through a main vein or artery into the interior region of the heart that is to be treated. The physician then further manipulates a steering mechanism to place the electrode carried on the distal tip of the catheter into direct contact with the endocardial tissue that is to be ablated. The physician directs energy from the electrode through tissue either to an indifferent electrode (in a uni-polar electrode arrangement) or to an adjacent electrode (in a bi-polar electrode arrangement) to ablate the tissue and form a lesion.

Physicians examine the propagation of electrical impulses in heart tissue to locate aberrant conductive pathways and to identify foci, which are ablated. The techniques used to analyze these pathways and locate foci are commonly called "mapping."

Conventional cardiac tissue mapping techniques use multiple electrodes positioned in contact with epicardial heart tissue to obtain multiple electrograms. These conventional mapping techniques require invasive open heart surgical techniques to position the electrodes on the epicardial surface of the heart.

An alternative technique of introducing multiple electrode arrays into the heart through vein or arterial accesses to map endocardial tissue is known. Compared to conventional, open heart mapping techniques, endocardial mapping techniques, being comparatively non-invasive, hold great promise. Still, widespread practice of endocardial mapping techniques has been hindered by the difficulties of making suitable endocardial electrode support structures, including severe size constraints, strength and durability demands, and the sheer complexities of fabrication.

An endocardial mapping structure can potentially remain in place within a heart chamber for several thousand heart beats. During this time, the powerful contractions of heart muscle constantly flex and stress the structure. The structure must be strong and flexible enough to keep the electrodes spaced apart both longitudinally and circumferentially without failure and without shed parts. In addition, there is also the need to provide simple, yet reliable ways of electrically coupling multiple electrodes to external sensing equipment. Still, though strong and durable, the structures must cause no trauma when in contact with tissue.

While prior multiple electrode support structures may attempt to provided the requisite strength and flexibility, they have created envelopes with blunt, non-conforming contours that can poke into tissue and cause trauma during heart contractions.

It can be seen that providing economical, durable, and safe multiple electrodes in a package small enough to be deployed within the heart often poses conflicting challenges.

SUMMARY OF THE INVENTION

This invention has as its principal objective the realization of safe and efficacious endocardial mapping techniques.

The invention provides multiple electrode assemblies that possess minimal structural parts and complexity, lending themselves to practical, economical fabrication techniques.

In providing these and other benefits, one aspect of the invention provides an electrode circuit having a distal region for carrying at least one electrode, a proximal region for connection to external apparatus, and an intermediate region electrically coupling the distal region with the proximal region. According to this aspect of the invention, at least one of the regions comprises flexible ribbon cable having two or more adjacent tracks of electrical conduction material and adjoining electrical insulating material.

In a preferred embodiment, all regions of the electrode circuit comprise a continuous length of ribbon cable. In this preferred arrangement, the distal region includes a region on at least one of the tracks where the conductive wire is exposed. An electrical conducting material overlies the region. The material is electrically coupled to the exposed conductive wire and comprises the electrode.

In a preferred embodiment, the electrode is deposited upon the region by sputtering, vapor deposition, or other appropriate technique. The deposited electrode is very thin, having a thickness of only about 5 to 200 microinches.

The direct deposition of the electrode on the ribbon cable provides highly dense, extremely reliable electrical connections. The act of depositing the electrode upon the ribbon cable itself electrically couples the exposed conductive wire to the deposited material. The deposited electrical connection site creates no discontinuities in mechanical properties, like those encountered using conventional soldering, spot welding, or other mechanical joining techniques. Because the deposited electrode is extremely thin at the electrical connection site, the electrode and associated electrical connection bend virtually without generating stress during handling, manipulation, and use. Furthermore, the deposition of the electrode provides an extremely reliable assembly process, lending itself to efficient mass production techniques, requiring minimal hand labor and manipulation.

In a preferred embodiment, a stiffener member supports the distal region of the ribbon cable and the overlying electrode. The stiffener member is connected to and constrained at opposite ends by a hub and a base, which urge the stiffener member into a predetermined curvilinear contour.

In an alternative embodiment, the distal region of the electrode circuit is carried upon a flexible substrate that includes the at least one electrode. In this embodiment, the intermediate and proximal regions include a length of flexible ribbon cable electrically coupled to the electrical circuit of the flexible substrate.

In this arrangement, a stiffener member preferably supports the flexible substrate. The stiffener member is connected to and constrained at opposite ends by a hub and a base to urge the stiffener member into a predetermined curvilinear contour.

Another aspect of the invention provides a catheter comprising a guide body having a proximal end and a distal end. A handle is attached to the proximal end of the guide body.

The catheter also includes an electrode assembly having a distal region carrying at least one electrode attached to the distal end of the guide body. The electrode assembly also includes an intermediate region extending from the distal region and carried by the guide body between its distal and proximal ends. The electrode assembly further includes a proximal region extending from the intermediate region and carried by the handle.

According to this aspect of the invention, a multiplexer is carried by the handle. The multiplexer includes an input electrically coupled to the proximal region of the electrode assembly in the handle. The multiplexer also includes an output electrically coupled to a connector member outside the handle.

In a preferred embodiment, the distal region, the proximal region, and the intermediate region of the electrode assembly include a continuous length of flexible ribbon cable comprising two or more adjacent tracks of electrical conduction material and adjoining electrical insulating material.

The highly dense, extremely reliable electrical connections that the ribbon cable provides obviates the need for a multiplexer at the distal regions of the catheter. Still, the presence of the multiplexer within the proximal handle reduces the number of connection pins the external connector carries. Thus, the external connector can be significantly less expensive, compared to a high density connector with a high number of pins.

Other features and advantages of the inventions are set forth in the following Description and Drawings, as well as in the appended Claims.

BRIEF DESCRIPTION OF THE DRAWINGS

FIG. 1A is a plan view of a multiple electrode probe that embodies the features of the invention, showing the associated electrode support assembly in its deployed condition;

FIG. 2 is an enlarged view of the distal end of the probe shown in FIG. 1A, showing the associated electrode support assembly in a collapsed condition within a sliding outer sleeve;

FIG. 10 is an exploded perspective view of the electrode support assembly assembled from several hoop-like bodies shown in FIG. 3 using the end cap shown in FIG. 5 and a base;

FIG. 11 is a lock ring associated with the base for the support assembly shown in FIG. 10, taken generally along line 11—11 in FIG. 10;

FIG. 12 is an exploded perspective view of the lock ring and anchor member of the base for the electrode support assembly shown in FIG. 10;

FIG. 13 is an assembled perspective view of the lock ring and anchor member of the base for the electrode support assembly shown in FIG. 10;

FIGS. 14 to 18 are top views of the fabrication of an electrode support assembly comprising spline elements and a web machined from a single sheet of material that embodies the features of the invention;

FIG. 19 is an enlarged view of the web of the electrode support assembly whose fabrication is shown in FIGS. 14 to 18;

FIGS. 23 and 24 are perspective views of the leaves and swaged pin assembled in FIG. 22, after over-molding of an end cap;

FIG. 38 is a perspective view of the assembly of the distal end of the electrode circuit assembly shown in FIG. 37 to the electrode support assembly shown in FIG. 10;

FIG. 39 is a side section view taken generally along line 39—39 in FIG. 38, showing Step 1 of assembling the distal end of the electrode circuit assembly shown in FIG. 37 to the electrode support assembly shown in FIG. 10;

FIG. 40 is a side section view taken generally along line 40—40 in FIG. 38, showing Step 2 of assembling the distal end of the electrode circuit assembly shown in FIG. 37 to the electrode support assembly shown in FIG. 10;

FIG. 41 is a side section view taken generally along line 41—41 in FIG. 38, showing Step 3 of assembling the distal end of the electrode circuit assembly shown in FIG. 37 to the electrode support assembly shown in FIG. 10;

FIG. 42 is a side section view of the electrode support assembly shown in FIG. 38 and associated distal end of the electrode circuit assembly shown in FIG. 37 mounted on the distal end of a catheter tube, with the intermediate portion of the electrode circuit assembly wrapped about the catheter tube;

FIG. 43 is a top view of the front surface of a flexible substrate used to form an electrode circuit assembly that embodies the features of the invention;

FIG. 44 is an enlarged view of a portion of the front surface of the substrate shown in FIG. 43, showing the details of one electrode pad deposited thereon;

FIG. 45 is a top view of the back surface of the flexible substrate shown in FIG. 43, showing the connection pads and traces deposited thereon;

FIG. 46 is an enlarged view of a portion of the back surface of the substrate shown in FIG. 45, showing the details of an alignment mark deposited thereon;

FIGS. 50 and 51 are side views showing the lacing of the electrode-carrying substrate and attached ribbon cable to an insulating sleeve;

FIG. 52 is a side perspective view showing the assembly of the interlaced substrate and sleeve shown in FIG. 51 to the electrode support structure shown in FIG. 10;

FIG. 53 is an enlarged side perspective view of the assembly shown in FIG. 52 mounted on the distal end of a catheter tube, with the intermediate portion of the electrode circuit assembly wrapped about the catheter tube;

FIG. 54 is a side view of the wrapping of the intermediate portion of the electrode circuit assembly about the catheter tube shown in FIG. 53;

Figure 1B:
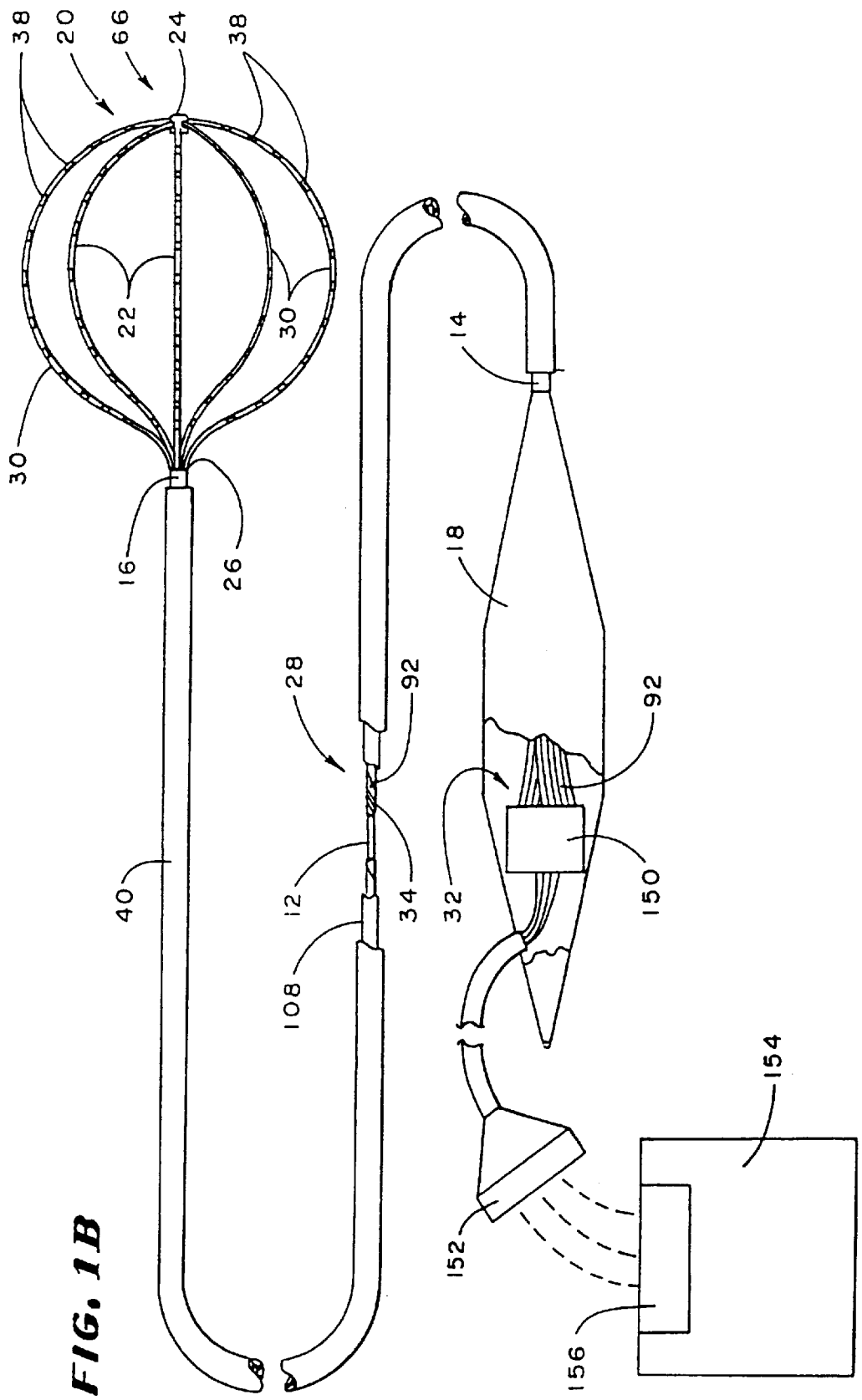
FIG. 1B is a plan view of an alternative construction of a multiple electrode probe that also embodies the features of the invention.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

FIG. 1A shows a multiple electrode probe 10 that embodies the features of the invention.

The probe 10 includes a flexible catheter tube 12 with a proximal end 14 and a distal end 16. The proximal end 14 carries an attached handle 18. The distal end 16 carries an electrode support assembly 20.

The electrode support assembly 20 comprises an array of flexible spline elements 22 assembled to form a three dimensional structure. The far ends of the spline elements 22 radiate from a distal hub. The near ends of the spline elements 22 are affixed to a base, which the distal end 16 of the catheter tube 12 carries.

Preferably, the spline elements 22 comprise thin, rectilinear strips of resilient metal or plastic material. Still, other cross sectional configurations can be used.

In the illustrated embodiments, the support assembly 20 retains the spline elements 22 in a three dimensional basket structure. Of course, the resulting structure can assume other shapes.

The probe 10 also includes an electrode circuit assembly 28, one for each spline 22. Each circuit assembly 28 includes a distal region 30 that contains one or more electrodes 38. Each circuit assembly 28 includes a proximal region 32 and an intermediate region 34.

The electrode-containing distal region 30 is carried by the associated spline 22. The proximal region 30 is electrically coupled within the handle 18 to one or more connectors 36 carried outside the handle 18. The intermediate region 34 is wrapped about the catheter tube 12.

When deployed for use (as FIG. 1A shows)—for example, inside a heart chamber—the support assembly 20 holds the electrodes 38 of the distal regions 30 in intimate contact against body tissue.

In the illustrated and preferred embodiment, the probe 10 includes an outer sheath 40 carried about the catheter tube 12. As FIG. 2 best shows, the sheath 40 has an inner diameter that is greater than the outer diameter of the catheter tube 12. As a result, the sheath 40 slides along the catheter tube 12.

As FIG. 2 shows, forward movement advances the slidable sheath 40 over the support assembly 20. In this position, the slidable sheath 40 compresses and collapses the support assembly 20 for introduction through a vein or artery to the intended treatment site within the body.

As FIG. 1A shows, rearward movement retracts the slidable sheath 40 away from the support assembly 20. This removes the compression force. The freed support assembly 20 opens and assumes its three dimensional shape.

A. The Support Assembly

The electrode support assembly 20 can be assembled in different ways. The drawings exemplify three embodiments.

(1) The Hoop Spline Assembly

FIGS. 3 to 13 show a preferred embodiment of a support assembly, identified by reference numeral 20(1).

In the assembly 20(1), two spline elements 22 are paired together in an integral body 42. Two or more spline bodies 22 are joined together to form the assembly 20(1).

Figure 3:
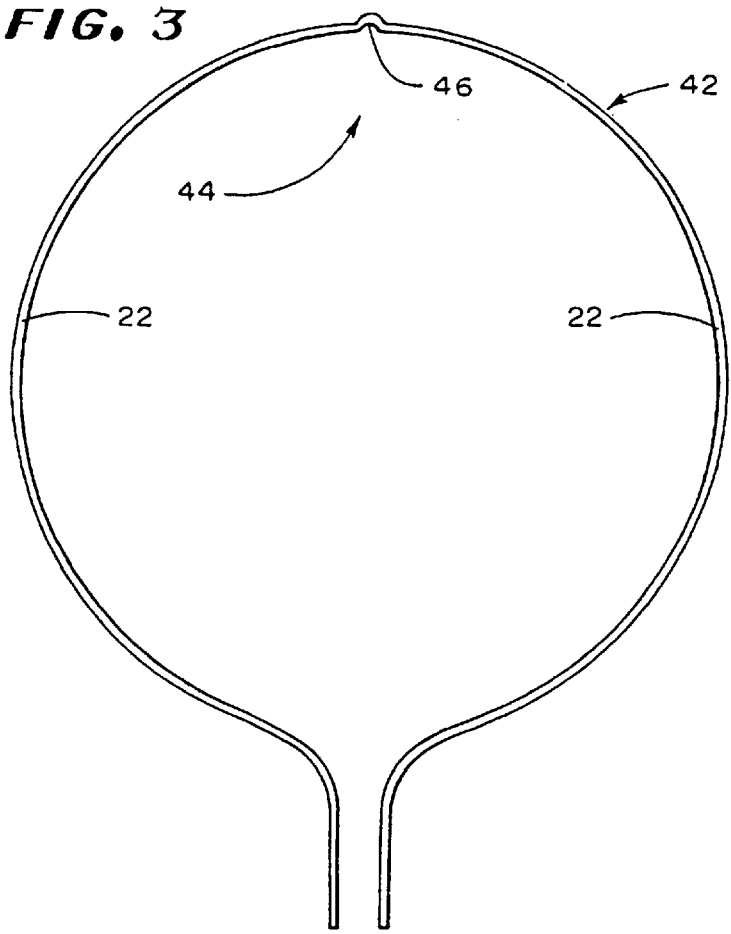
FIG. 3 is an elevation view of an integral, hoop-like body that can be assembled to form an electrode support assembly that embodies the features of the invention.
Figure 4:
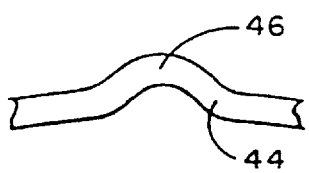
FIG. 4 is an enlarged view of the mid-section of the hoop-like body shown in FIG. 3, showing the detent used to lock the body into an associated end cap.

Each body 42 includes a mid-section 44 from which the spline elements 22 extend as an opposed pair of legs. In this arrangement, the body 42 is generally shaped like a hoop (see FIG. 3). As FIGS. 3 and 4 show, the mid-section 44 includes a preformed notch or detent, whose function will be described later.

The hoop-like body 42 is preferably made from resilient, inert wire, like Nickel Titanium (commercially available as Nitinol material). However, resilient injection molded inert plastic or stainless steel can also be used.

Figure 5:
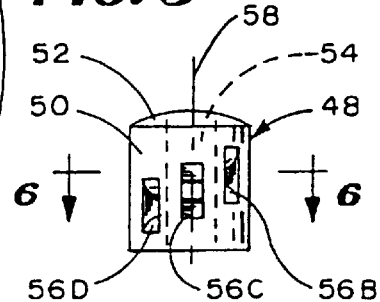
FIG. 5 is a side elevation view of the end cap used to assemble the hoop-like body shown in FIG. 3 into an electrode support assembly.
Figure 6:
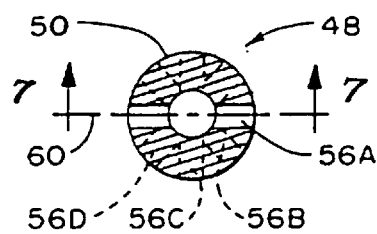
FIG. 6. is a top section view of the end cap taken generally along line 6—6 in FIG. 5.
Figure 7:
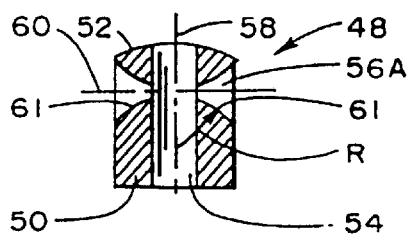
FIG. 7 is a side section view of the end cap taken generally along lines 7—7 in FIG. 6.

In this embodiment, the distal hub 24 comprises an end cap 48 (see FIG. 10). As FIGS. 5 to 7 show, the end cap 48 has a generally cylindrical side wall 50 and a rounded end wall 52. A longitudinal bore 54 extends through center the cap 48.

Slots 56A; 56B; 56C; and 56D extend through the cap 48 diametrically across the center bore 54. The number of slots can vary. In the illustrated embodiment, there are four through-slots 56A–D.

The slots 56A–D are circumferentially spaced about the axis 58 of the bore 54. The axis 60 of each slot 56A–D extends diametrically through the center axis 58 (see FIGS. 6 and 7), passing through the center bore 54.

The slot axes 60 are also spaced longitudinally along the bore axis 54. The resulting staggered pattern of slots 56A–D is both circumferentially and longitudinally spaced along each 180° segment of the hub 48 (see FIGS. 9 and 10). As FIG. 10 best shows, slot 56A is closest to the end wall 52. The slot 56D is farthest from the end wall 52. Intermediately slots 56B and 56C are sequentially spaced in between the slots 56A and 56D.

In the illustrated and preferred embodiment, the cap 48 is made of an inert, machined metal, like stainless steel. The bore 54 and slots 56A–D are preferably formed by conventional EDM techniques. Still, inert molded plastic materials can be used to form the cap 48 and associated openings.

A spline leg 22 of the hoop-like body 42 can be inserted through a slot 56A–D until the mid-body section 44 enters the bore 54. The detent 46 snaps into the bore 54 to lock the body 42 to the end cap 48, with the opposed pair of spline legs 22 on the body 42 radiating free of the respective slot 56A–D. Sequentially inserting the four hoop-like bodies 42 in the four slots 56A–D orients and locks the spline elements 22 in the radiating pattern shown in FIG. 10. The three dimension support assembly 20(1) shown in FIG. 10 results.

In the support assembly 20(1), the base 26 includes an anchor member 62 and a mating lock ring 64 (see FIGS. 10 to 13). The anchor member 62 fits with an interference friction fit into the distal end 16 of the catheter tube 12. The lock ring 64 includes a series of circumferentially spaced grooves 66 into which the free ends of the spline legs 22 fit. The lock ring 64 fits about the anchor member 62 to capture with an interference fit the free ends of the spline legs 22 between the interior surface of the grooves 66 and the outer surface of the anchor member 62 (see FIG. 13). The anchor member 62/lock ring 64 assembly holds the spline elements 22 in a desired flexed condition.

The hoop-like body 42, slotted end cap 48, and anchor member 62/lock ring 64 assembly minimize the number of the components parts required to form the support assembly 20(1). The slotted cap 48 circumferentially aligns and stabilizes the spline elements 22, both circumferentially and longitudinally. The sequential insert-and-lock process of the attaching the bodies 42 to the slotted cap 48 also significantly simplifies the assembly process.

Figure 9A:
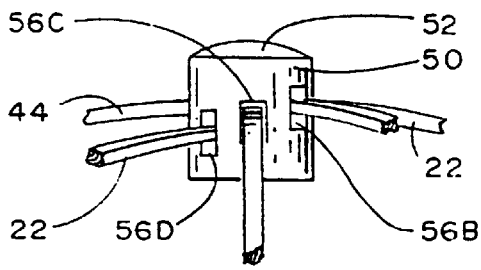
FIG. 9A is a side elevation view of the end cap shown in FIG. 5 with multiple hoop-like bodies shown in FIG. 3 secured in place to form an electrode support assembly.
Figure 9B:
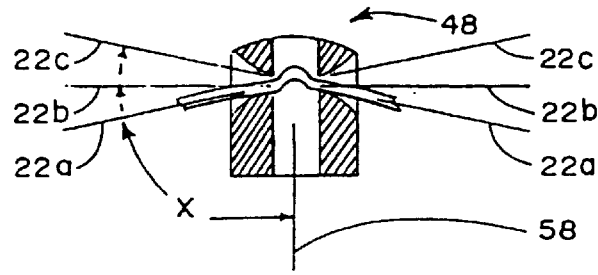
FIG. 9B is a diagrammatic view of the end cap shown in FIG. 5, demonstrating the preferred angular relationship between the spline elements and the end cap.

The spline elements 22 extend through the axis of the cap 48 at an angle χ (see FIG. 9B) that is greater than about 45° (as shown by phantom line spline elements 22a in FIG. 9B), but is less than about 110° (as shown by phantom line spline elements 22c in FIG. 9B). Preferably, the angle χ is between about 80° and 100°. In the illustrated preferred embodiment (as shown by spline elements 22b in FIG. 9B), the angle χ is about 90° (i.e., the spline elements 22c extend generally perpendicular to the axis of the cap 48).

As FIG. 10 shows, the angle χ that the cap 48 imposes creates an oval support structure 20(1) having a curvature that best approximates the contour of endocardial heart tissue. The oval structure 20(1) includes an enlarged, dome-shaped distal surface area 66 (see FIGS. 1 and 10). The surface area 66 conforms intimately to endocardial tissue as the heart beats. The slotted cap 48 supports the distal ends of the spline elements 22 without imposing reverse or compound bends that force the spline elements 22 inward, out of the natural contour of heart tissue.

The slotted structure of the cap 48 makes possible the location of the distal-most spline elements 22 very close to the distal end of the cap 48. In the illustrated and preferred embodiment, the most distal slot 56A, through which the distal-most spline elements 22 extend, has a centerline that is separated from the distal end of the cap 48 by no more than about 0.040".

As a result (see FIG. 10), when the structure 20(1) is fully deployed for use, the cap 48 projects only a minimal distance beyond the envelope of the resulting structure 20(1). Practically speaking, the cap 48 lies essentially within the envelope of the distal surface area 66.

The geometry that the cap 48 permits creates a relatively smooth surface area 66 that is essentially free of major projections that can extend to a significant extent into endocardial tissue. The contour of the surface 66 extends along an essentially constant arc from one spline 22, across the end cap 48 to an opposite spline 22. The end cap 48 presents a surface 66 free of outward physiologically significant projections that can poke endocardial tissue to cause blunt tissue trauma. The contoured surface 66 extending about the cap 48 thus minimizes the chances of damage to endocardial tissue during use.

The contoured surface 66 permits access to and intimate contact with tissue in the apex of the heart, at the base of the ventricles. About 20% of infarcted heart tissue is found to lie within the apex. Therefore, providing non-traumatic access to this region offers considerable therapeutic benefit.

Furthermore, the alignment of the end cap 48 along this contoured surface 66 makes it possible to use the end-cap 48 itself as an electrode. The contour surface 66 and non-projecting end-cap 48 allow the physician to deploy the structure 20(1) and obtain electrogram signals from the apex of the heart using the end-cap as an electrode. Again, considerable therapeutic benefits result.

Figure 8:
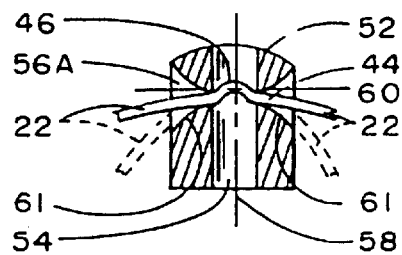
FIG. 8 is a side section view showing the mid-section of a hoop-like body shown in FIG. 4 locked in place within the end cap shown in FIG. 5.

In the illustrated and preferred embodiment, the lower surface 61 of the end cap slots 56 is curved (see FIGS. 7 and 8). The curved lower surface 61 contacts the spline elements 22 (see FIG. 8) when then are bent, or deflected, a prescribed amount. The curvature of the lower slot surface is selected to lend positive support to the spline elements 22 when bent this amount, as FIG. 8 shows. The positive support of the surface 61 prevents spline deflection beyond a minimum bend radius. The bend radius is selected to be above that which failure-mode stresses are most likely to develop in the spline elements 22.

In the illustrated embodiment, failure mode stresses are most likely to occur when the slidable sheath 40 compresses and collapses the spline elements 22. The preservation of a minimum bend radius that the cap 48 furnishes prevents sharp bends and failure-mode stresses to develop when the spline elements 22 are collapsed into their most stressed position.

The specific minimum bend radius selected depends upon the material from which the spline elements 22 are made and the thickness of the spline elements 22. In the preferred embodiment, which uses Nitinol spline elements 22 with a thickness of about 0.007", the minimum bend radius imposed by the surface 61(shown as radius R in FIG. 7) is about 0.025".

The physical characteristics of the support structure 20(1) can be modified by altering the width and/or thickness of the associated spline elements 22.

The width of the spline elements 22 effects the number of spline elements 22 that the structure 20(1) can accommodate, particularly when collapsed. By reducing the width of individual spline elements 22, the collapsible structure 20(1) can accommodate more spline elements 22. Since the circumferential spacing of the spline elements 22 is least near the cap 48, the spline elements 22 can be locally thinned in this region, when desired, to present a compact geometry that accommodates the collapsing of multiple, closely spaced spline elements 22.

The thickness of the spline elements 22 effects flexibility and the magnitude of the stress developed during flexing. Thinning the spline element 22 imparts greater flexibility, while at the same time reducing the magnitude of the stress developed during flexing. Since greatest stress upon flexing occurs near the cap 48 (where the greatest degree of bending occurs), the spline elements 22 can be locally thinned in this region, when desired, to impart greater resistance to stress failure.

The localized reductions of width and/or thickness also reduces force required to collapse the structure 20(1).

(2) Integrated Spline Assembly

Figure 20:
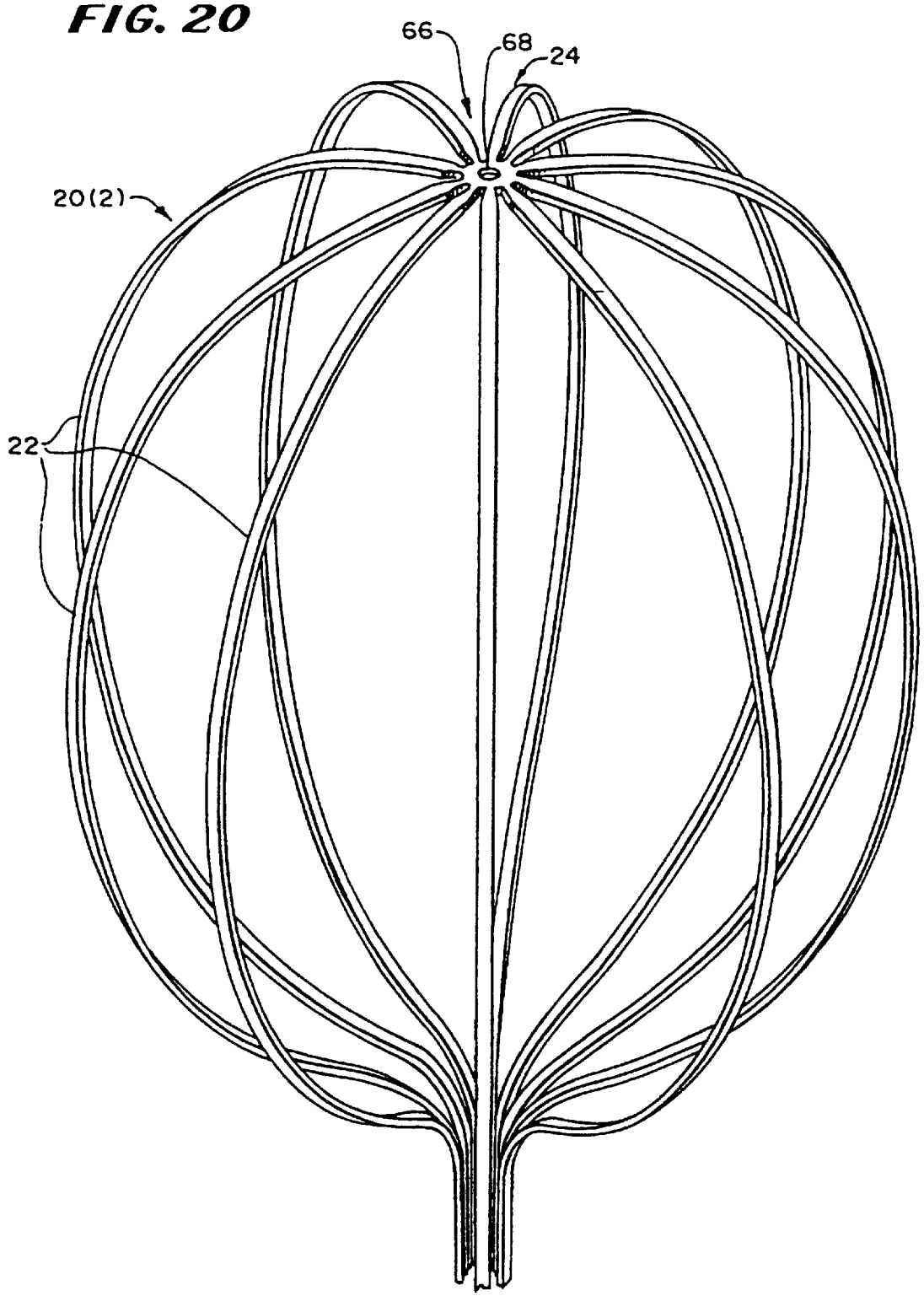
FIG. 20 is a perspective view of the electrode support assembly shown in FIG. 18, when flexed to form a three dimensional electrode support structure.

FIGS. 20 shows an alternative embodiment of a support assembly, designated by reference numeral 20(2).

The support assembly 20(2) includes spline elements 22 radiating in a circumferentially spaced relationship from a center web 68, which constitutes the hub 24. As FIGS. 14 to 19 show, the spline elements 22 and web 68 are machined from a single sheet 70 of material.

Figure 14:
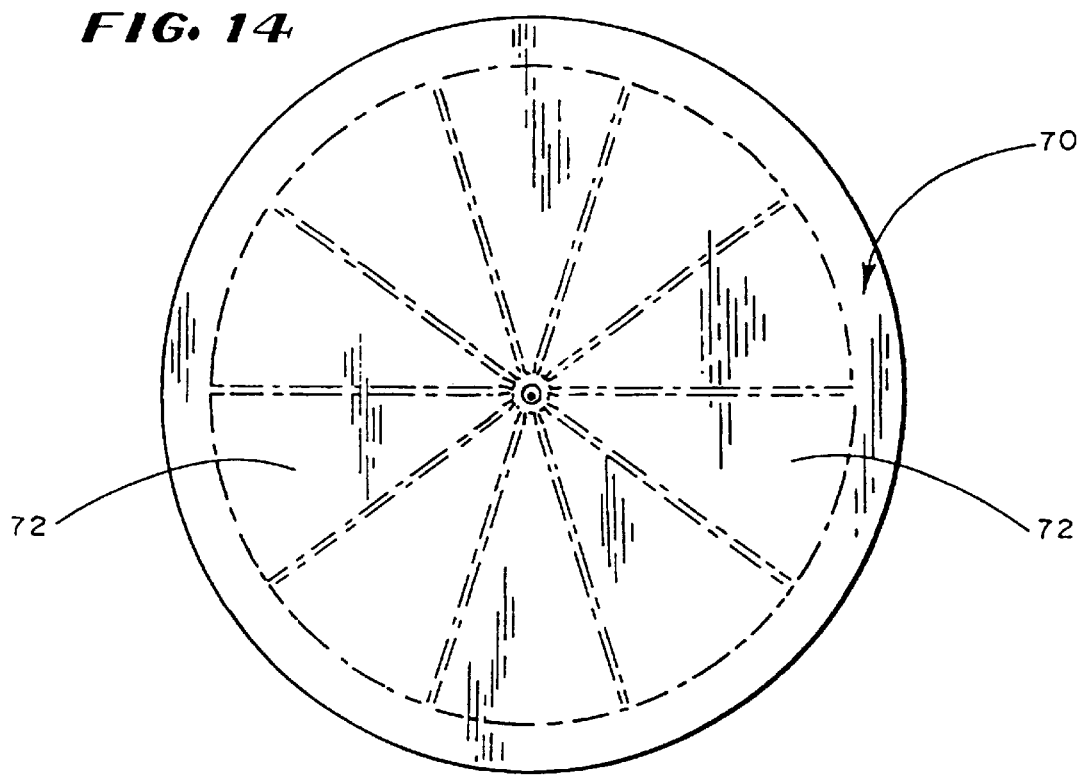

As FIG. 14 shows, the sheet 70 comprises Nickle Titanium stock having a thickness of about 0.004 inch. Other materials, like extruded or molded plastic, or stainless steel can be used for the sheet.

Figure 15:
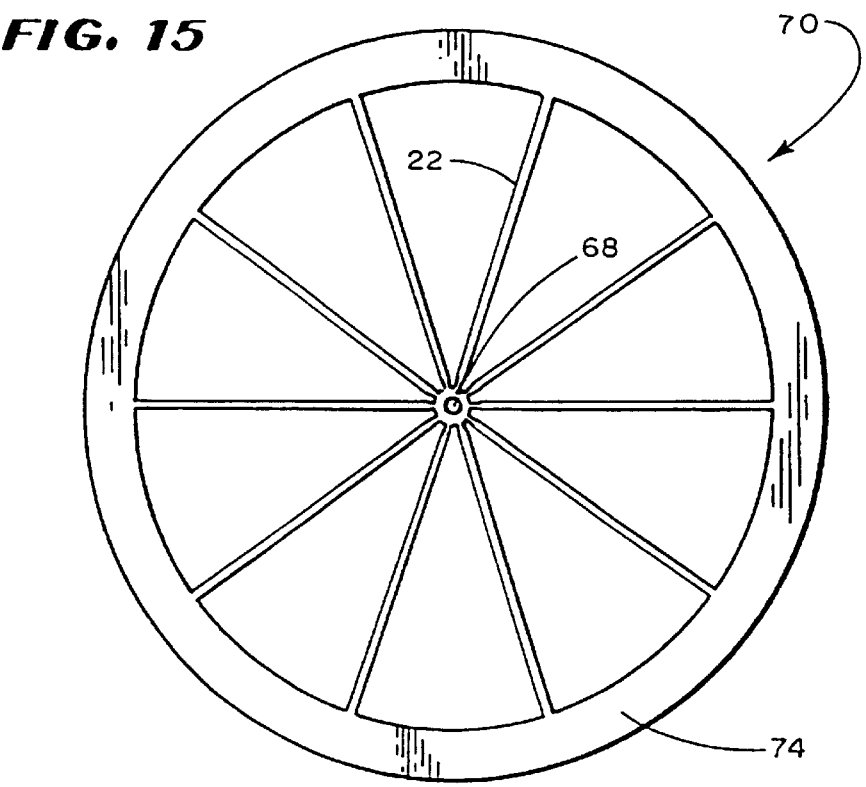

As FIGS. 14 and 15 show, circumferentially spaced, pie shaped segments 72 are initially cut from the sheet 70, leaving behind the spline elements 22 having the desired width and circumferential spacing. One end of the spline elements 22 are connected to the web 68, from which they radiate like spokes. The other end of the spline elements 22 are connected to a remaining rim 64 of material.

Next, as FIGS, 16 and 17 show, the rim 74 of material is cut away from the spline elements 22, leaving only the spline elements 22 and web 68 remaining (see FIG. 18).

Laser cutting or another accurate, mechanized cutting technique, like EDM, can be used for this purpose.

As FIG. 19 shows, each spline 22 is cut to include a tapered region 76 of reduced width near the web 68. This region 76 permits the inclusion of more spline elements 22. If desired, the region 76 can also present a reduced thickness to impart greater flexibility to the spline elements 22 near the web 68, without otherwise detracting from the mechanical strength of the rest of the spline elements 22. Localized reductions of width and/or thickness also reduces force required to collapse the structure 20(2).

As FIG. 20 shows, the spline elements 22 are bent relative to the web 68 to form the desired three dimensional shape of the assembly 20(2). The free ends of the spline elements 22 can be joined to an anchor member 62/locking ring 64 assembly, as before described.

As FIG. 20 shows, the spline elements 22 extend from the web 68 generally perpendicular to the axis of the web. The support structure 20(2), like the structure 20(1), assumes an oval curvature that approximates the contour of endocardial heart tissue.

Like the structure 20(1), the oval structure 20(2) includes an enlarged, dome-shaped distal surface area 66 (see FIG. 20), which conforms intimately to endocardial tissue as the heart beats. The spline elements 22, being an integral part of the web 68, include no reverse or compound bends at their junction with the web 68.

When the integrated structure 20(2) is fully deployed for use (as FIG. 20 shows), the web 68 lies within the envelope of the distal surface area 66. The contour of the surface 66 extends along an essentially constant arc from one spline element 22, across the web 68 to an opposite spline element 22. The surface 66 is free of outward, physiologically significant projections that can poke endocardial tissue to cause blunt tissue trauma. The contoured surface 66 of the integrated structure 20(2) thus minimizes the chances of damage to endocardial tissue during use. The contoured surface 66 also permits access to and intimate contact with tissue in the apex of the heart, at the base of the ventricles.

The integrated assembly 20(2) also provides a precise geometry that can be accurately machined. It simplifies the manufacture of a support assemblies 20 having multiple spline elements 22.

(3) Pinned Spline Assembly

FIGS. 21 to 24 show yet another alternative embodiment of a support assembly, identified by reference numeral 20(3).

Figure 21:
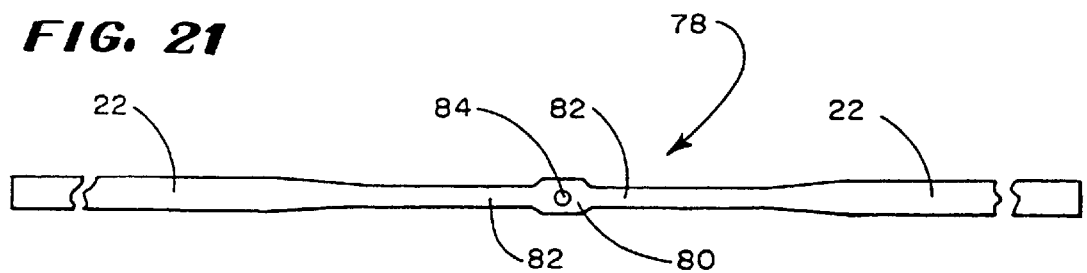
FIG. 21 is a top view of an integral leaf having opposed spline elements and a connecting web that can be assembled to form an electrode support assembly that embodies the features of the invention.

In the assembly 20(3), two spline elements 22 are paired together in an integral leaf 78 (see FIG. 21). Two or more leaves 78 are joined together to form the assembly 20(3)(see FIGS. 22 and 24).

Each leaf 78 includes a center web 80 that joins the spline elements 22 together in a diametrically opposed pair. The web 80 includes a drilled hole 84 located along the centerline and equidistant from the ends of each leaf 78.

Figure 22:
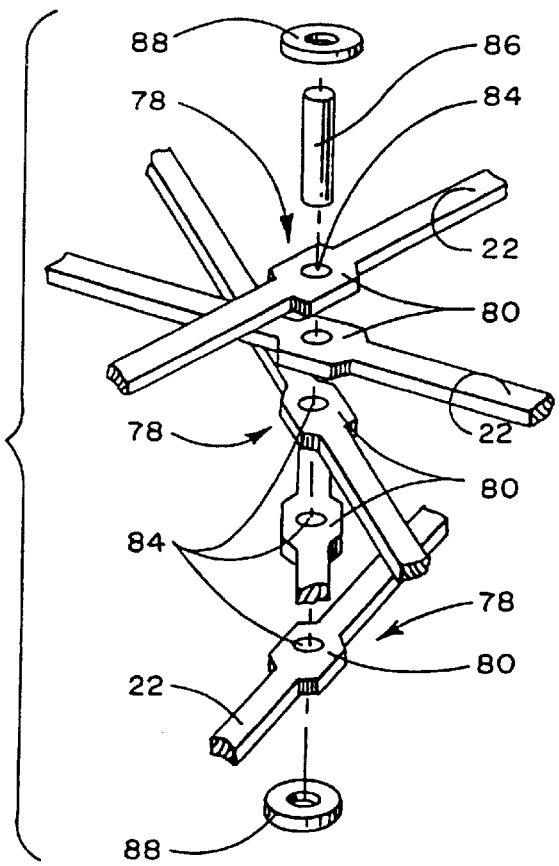
FIG. 22 is an exploded perspective view of the assembly of several integral leaves shown in FIG. 21 about a swaged pin.

As FIG. 22 shows, the leaves 78 are assembled in a stacked relationship about a center pin 86 that extends through the web holes 84. In the illustrated embodiment, the pin 86 holds five leaves 78. The leaves 78 are aligned at the pin 86 in an equal circumferentially spaced array comprising ten spline elements. The leaves 78 are swaged together in this array between two washers 88.

Next, a hub 90 of inert plastic or elastomeric material, like silicone, is over-mold about the swaged pin 86 and washers 88. The over-molded hub 90 fixes and preserves the desired angular array of the leaves 78.

As FIG. 24 shows, after the hub 90 has been over-molded, the spline elements 22 can be resiliently flexed into the desired three dimensional shapes. As FIG. 21 shows, the web 80 preferably presents a region 82 of reduced width near the hub 90. This region 82 permits the inclusion of more spline elements 22. If desired, the region 82 can also present a reduced thickness to impart greater flexibility to the spline elements 22 near the hub 90, without otherwise detracting from the mechanical strength of the rest of the spline elements 22. Localized reductions of width and/or thickness also reduces force required to collapse the structure 20(3).

Once fashioned into the desired shape, the free ends of the spline elements 22 of the structure 20(3) can be joined to an anchor member 62/locking ring 64 assembly, as before described.

As FIGS. 23 and 24 show, the spline elements 22 extend generally perpendicularly from the swaged pin 86 and washers 88, which represent the axis of the hub 90. The hub 90 thus creates an oval support structure 20(3) like structures 20(1) and 20(2), approximating the contour of endocardial heart tissue. Like structures 20(1) and 20(2), the structure 20(3) includes an enlarged, dome-shaped distal surface area 66 (see FIGS. 22 and 24), which conforms intimately to endocardial tissue as the heart beats. Like slotted cap 48, the over-molded hub 90 supports the distal ends of the spline elements 22 without imposing reverse or compound bends that force the spline elements 22 inward, out of the natural contour of heart tissue.

Like the slotted cap 48, the over-molded structure of the hub 90 makes possible the location of the distal-most spline elements 22 very close to the distal end of the cap 48, e.g. less than about 0.040" between them. As a result (see FIG. 24), when the structure 20(3) is fully deployed for use, the hub 90 projects only a minimal distance beyond the envelope of the resulting structure 20(3).

Like the slotted cap 48, the geometry that the over-molded hub 90 creates presents a relatively smooth surface area 66 that is essentially free of major projections that can extend to a significant extent into endocardial tissue. The contour of the surface 66 extends along an essentially constant arc from one spline element 22, across the hub 90 to an opposite spline element 22. The hub 90, like the end cap 48, presents a surface 66 free of outward physiologically significant projections that can poke endocardial tissue to cause blunt tissue trauma. The contoured surface 66 extending about the hub 90 thus minimizes the chances of damage to endocardial tissue during use. The contoured surface 66 also permits access to and intimate contact with tissue in the apex of the heart, at the base of the ventricles.

The over-molded hub 90 also lends positive support to the spline elements 22 when bent into a collapsed position to prevent spline deflection beyond a minimum bend radius. The bend radius is selected to be above that which failure-mode stresses are most likely to develop in the spline elements 22.

The over-molded hub 90 allows the use of spline elements 22 having a greater width to maximize the surface area of the resulting basket structure.

B. The Electrode Assembly

Regardless of their particular structure, the support assemblies 20(1); 20(2); and 20(3) are suitable for carrying electrode circuit assemblies 28, which can be assembled in various ways.

(1) Ribbon Cable Electrode Circuit

FIGS. 25 to 37 show a preferred embodiment for an electrode circuit assembly, which is identified by reference numeral 28(1) in FIG. 38.

Figure 25:
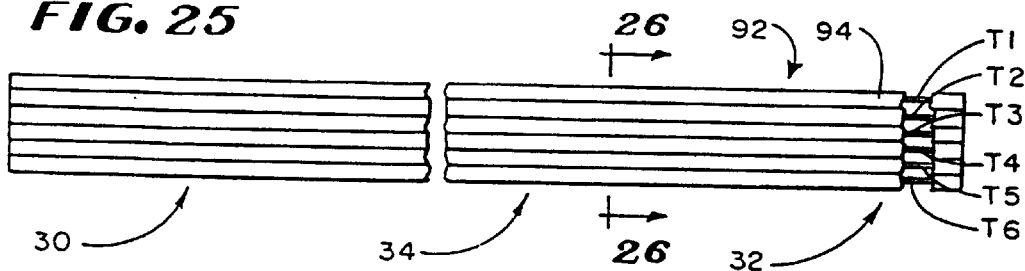
FIG. 25 is a top view of a continuous length of ribbon cable that is used to form an electrode circuit assembly that embodies the features of the invention.
Figure 26:
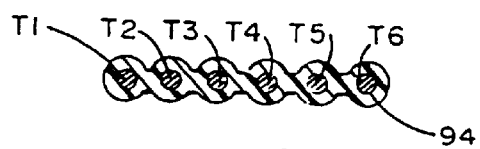
FIG. 26 is a side section view of the ribbon cable taken generally along line 26—26 in FIG. 25.

The assembly 28(1) includes one or more continuous lengths miniature, multi-conductor ribbon cable 92 (see FIGS. 25 and 26). The ribbon cable 92 includes parallel tracks of electrical conductive wire, designated T1 to T6 in FIGS. 25 and 26. The conductive wires T1 to T6 are overlaid with an electrical insulating material 94 (see FIG. 26), so that the tracks T1 to T6 are normally insulated one from the other.

Miniature, multi-conductor ribbon cable 92 can be commercially purchased from Temp-Flex Cable, South Grafton, Mass. The cable shown in the preferred embodiment (in FIGS. 25 and 26) comprises six tracks of 46 AWG bare copper wire (CT37 Alloy), overlaid by electrical insulation PFE material. With insulation, each track measures about 0.0037 inch in outside diameter, with a center-to-center distance of about 0.0039 inch. The overall width of the 6 track cable is about 0.025 inch. The cable has a D.C. resistance of about 6 ohms per foot; a voltage rating of about 100 volts; and a temperature rating of between about −65° C. to about 150° C.

The electrical circuit 28(1) uses two ribbon cables 92, each having six conductive tracks T1 to T6. Of course, more or fewer tracks can be used, depending upon the overall size limitations imposed.

The ribbon cables 92 themselves make up the distal region 30, the proximal region 32, and the intermediate region 34 of the circuit assembly 28(1).

Figure 27:
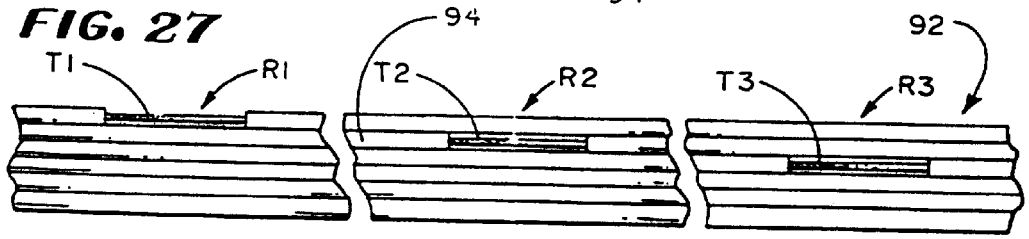
FIGS. 27 and 28 are top views showing the exposure of regions of electrical conduction wire in the ribbon cable shown in FIG. 25 in preparation for forming electrode bands on the distal end of the cable.
Figure 28:
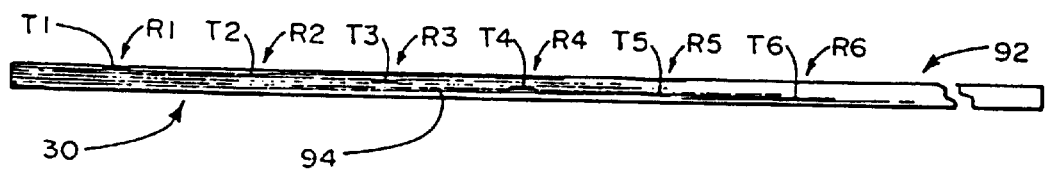

As FIGS. 27 and 28 show, the distal region 30 of each cable 92 used in the assembly 28(1)is first exposed to focused laser energy or similar technique to selectively remove a section of insulating material along small regions of the tracks T1 to T6, which are designated R1 to R6 in FIGS. 27 and 28. The exposed regions R1 to R6 are spaced axially from each other from one adjacent track to another.

In the illustrated embodiment, each region R1 to R6 measures about 0.035 inch in axial length. The axial spacing between each region measures about 0.177 inch. The removal of insulating material from each region exposes a portion of the underlying electrical conducting wire T1 to T6.

Figure 29:
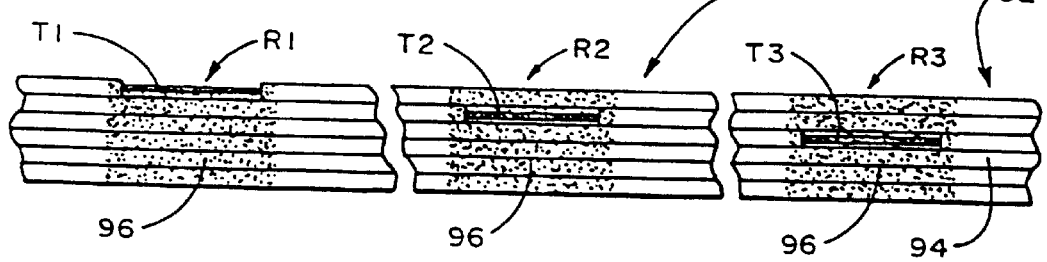
FIGS. 29 and 30 are top views showing the deposition of electrical conducting material on the exposed regions shown in FIGS. 27 and 28 to form the electrode bands on the distal end of the ribbon cable.
Figure 30:
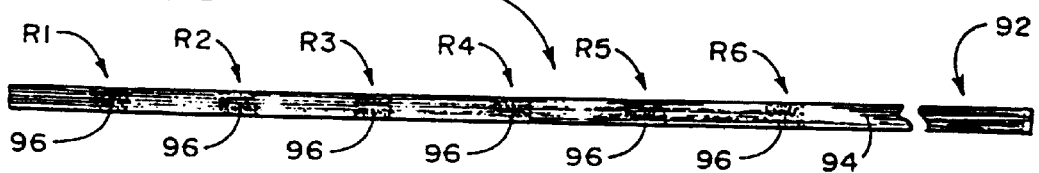

Next, as FIGS. 29 and 30 show, a band 96 of electrical conducting material is deposited across the width of the ribbon cable 92 over each exposed region R1 to R6. The band 96 is applied by sputtering, vapor deposition, or other appropriate technique.

In the preferred embodiment, each electrode band 96 comprises an undercoat deposition of titanium, followed by an overcoat deposition of platinum. The titanium undercoat provides better adherence to the platinum overcoat.

In an alternate embodiment, an alloy of platinum and iridium (90% Pt/10% Ir) is deposited to form each electrode band 96.

In either embodiment, each electrode band 96 that is about 0.045 inch in width and about 5 to 200 microinches thick. Thinner depositions provide less stress generation, but thinner depositions lead to greater ohmic resistance. Selecting the thickness requires a balancing of stress generation and ohmic resistance. In the preferred embodiment, each electrode band 96 has a thickness of about 100 microinches.

The act of depositing the band 96 electrically couples the electrical conducting wire T1 to T6 exposed in each region R1 to R6 to the band 96. The deposited bands 96 form spaced electrodes, one electrode electrically coupled to each conductive track T1 to T6 of the cable 92.

The deposition of electrode bands 96 upon the ribbon cable 92 provides an extremely reliable assembly process. Ribbon cables 92 with deposited electrode bands 96 can be prefabricated using efficient mass production techniques, requiring minimal hand labor. The electrical connections are not individually made by hand, thereby avoiding variabilities caused by human error and inattention. Significant improvements in both production economies and quality result.

Because the electrode bands 96 are deposited directly on the ribbon cable 92, the resulting electrical connection sites are robust. There are no discontinuities in mechanical properties, like those encountered using conventional soldering, spot welding, or other mechanical joining techniques.

Because the deposited electrode bands 96 are extremely thin at the electrical connection site (i.e., they are measured in microinches), they do not generate appreciable stress upon flexing. The electrode bands 96 and associated electrical connections bend virtually without generating stress during handling, manipulation, and use.

The direct deposition of the electrode bands 96 on the ribbon cable 92 provides highly dense, extremely reliable electrical connections that eliminate the need for multiplexing and other expensive techniques at the distal end of the catheter tube, aimed at reducing the number of mechanical electrical connections. The direct deposition of electrode bands 96 upon the ribbon cable 92 provides an electrode assembly 28(1) free of any mechanical connections between electrodes and electrical conduction wire.

As FIG. 38 shows, the circuit assembly 28(1) includes an electrical insulating sleeve 98. The sleeve 98 encloses the distal regions 30 of the two ribbon cables 92, except for their applied electrode bands 96. The electrode bands 96 (of which there are a total of twelve in FIG. 38) project through windows 100 in the sleeve 98.

In the illustrated and preferred embodiment (as FIGS. 31 to 37 show), the distal ends 30 of two ribbon cables 92 are placed within the sleeve 98 by lacing the ribbon cables 92 through the sleeve windows 100. This marries the cables 92 to the sleeve 92, while exposing the electrode bands 92.

For the sake of description, the distal ends of the two ribbon cables laced through the sleeve 98 are designated C1 and C2 in FIGS. 31 to 37. The sleeve windows 100 are also consecutively numbered W1 to W12 from the most distal end of the sleeve 98 to its most proximal end.

In assembly (see FIG. 31), the sleeve 98 is held by a mandrel (not shown) and cut by blades (also not shown) to form a series of spaced apart slits 102 in the peripheral surface of the sleeve 98. The slits 102 extend across the axis of the sleeve 98 for about 40% to 50% of the peripheral surface of the sleeve 98 in a pattern of closely spaced pairs. The windows 100 (also numbered W1 to W12) occupy the space between adjacent slits 102. As FIG. 31 shows, the sleeve material within each window 100 (W1 to W12) is not removed.

The length of each window 100 (W1 to W12) corresponds with the length of each electrode band 92. The spacing between the windows 100 corresponds with the distance between each electrode band 92.

Figure 31:
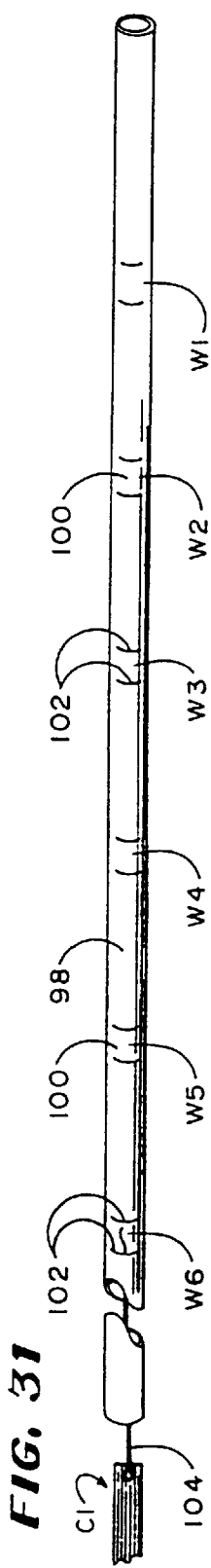
FIGS. 31 to 34 are side views showing the lacing of the distal end of a first ribbon cable into an insulating sleeve.
Figure 32:
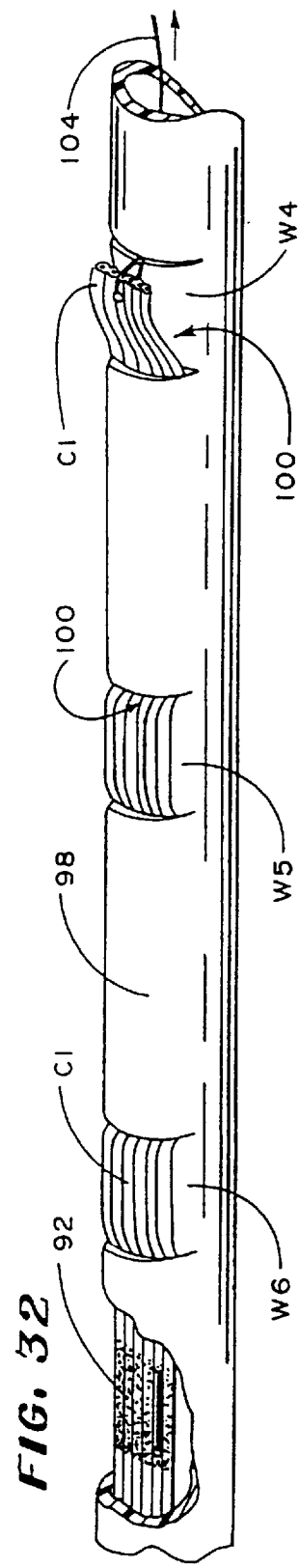
Figure 33:
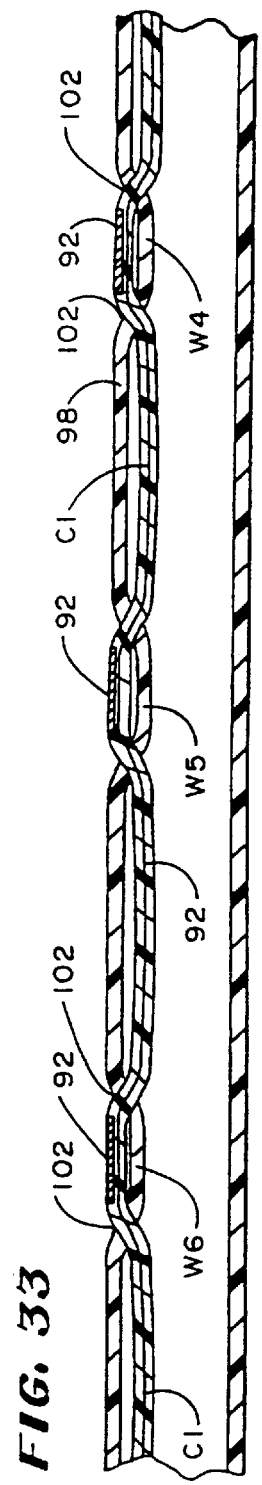

As FIGS. 31 to 32 show, a guide wire 104 is fastened to the end of the first ribbon cable C1. The guide wire is passed into the bore of the sleeve 98. Beginning with the pair of slits 102 that frame the sixth window W6, the wire 104 is threaded up and through the slits 102, passing over the sleeve material between the slits 102. The ribbon cable C1 follows (as FIG. 32 shows).

Figure 34:
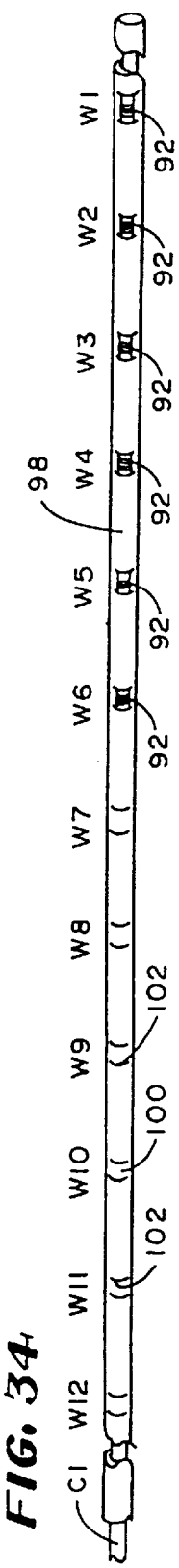

This progression laces the distal end 30 of the first ribbon cable C1 through the six most distal windows W1 to W6 of the sleeve 98 (as FIG. 34 shows). The six electrode bands 92 of the first ribbon cable C1 project through these six most distal windows W1 to W6 (see FIGS. 33 and 34). The remainder of the first ribbon cable C1 passes through the bore of the sleeve 98 and out its proximal end (as FIG. 34 shows).

Figure 35:
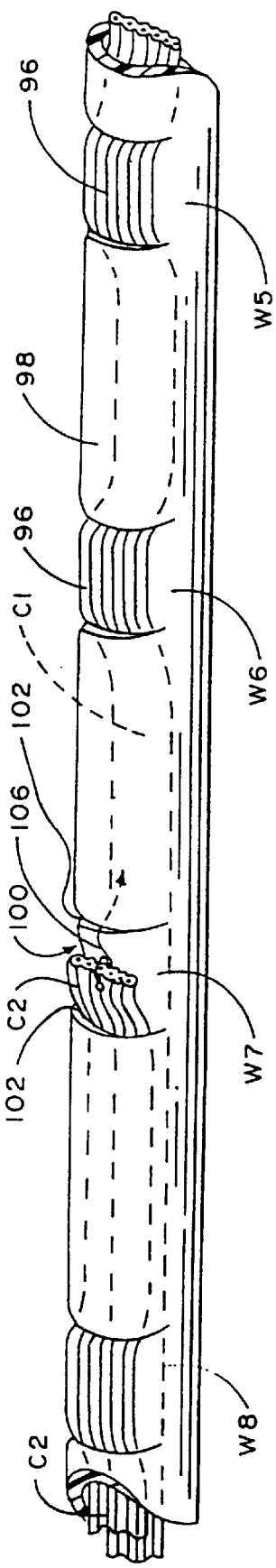
FIGS. 35 to 36 are side views showing the lacing of a second ribbon cable to the sleeve shown in FIGS. 31 to 34.
Figure 36:
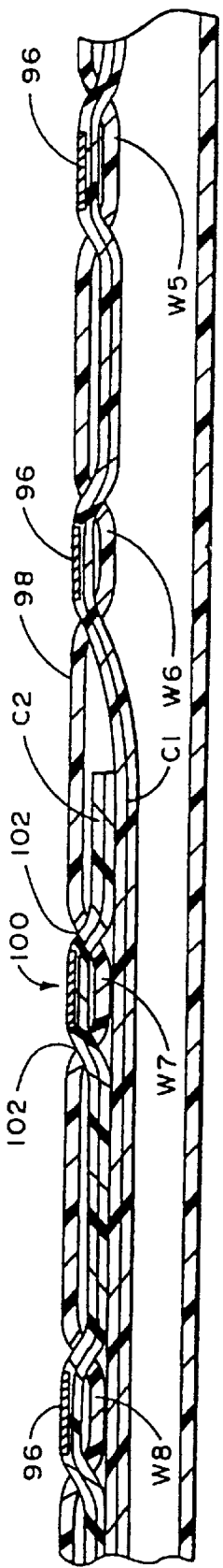

After lacing the first ribbon cable C1 to the sleeve 98, a guide wire 106 is fastened to the end of the second ribbon cable C2. The guide wire 106 is passed into the bore of the sleeve 98 over the first ribbon cable C1. Beginning with the pair of slits 102 that frame the most proximal window W12, the wire 106 is threaded up and through the slits 102 in succession, passing over the sleeve material between the slits 102. The ribbon cable C2 follows (as FIG. 35 shows) as the wire 106 is threaded up and through slits 102 of windows W12 to W7 (as FIGS. 35 to 37 show).

Figure 37:
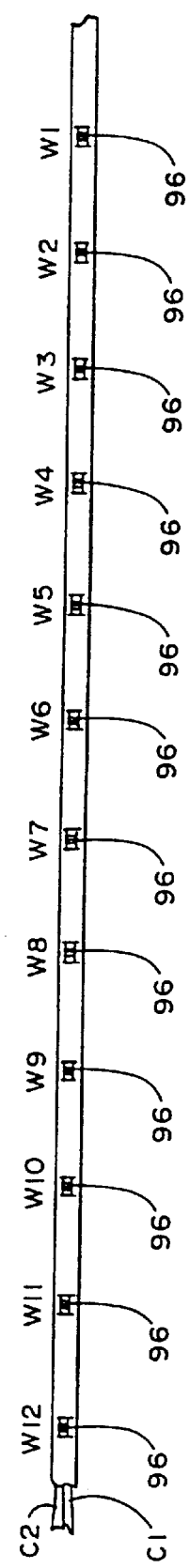
FIG. 37 is an interlaced assembly of two ribbon cables and the insulating sleeve forming the distal end of an electrode circuit assembly that embodies the features of the invention.

This progression laces the distal end 30 of the second ribbon cable C2 through the six most proximal windows W12 to W7 of the sleeve 98 (as FIG. 37 shows). The six electrode bands 92 of the second ribbon cable C2 project through these six most proximal windows W12 to W7. The remainder of the second ribbon cable C2 passes through the bore of the sleeve and out its proximal end (as FIG. 37 shows).

As FIG. 38 shows, the interlaced distal region 30 of sleeve 98 and ribbon cables C1 and C2 slides onto the spline elements 22 of the associated support assembly 20(1). The progression of sliding the interlaced distal region 30 onto the spline elements 22 is shown as Step 1; Step 2; and Step 3 in FIG. 38. This progression is also shown in side section in FIGS. 39, 40, and 41, respectively.

Steps 1, 2, and 3 occur before the free ends of the spline elements 22 are fastened to the anchor member 62/lock ring 64 assembly. During assembly, the electrode bands 96 are aligned to face outward on the spline elements (as FIG. 38 shows). These steps are repeated, until all spline elements contains the interlaced distal region 30.

The sleeve 98 is made of a material that is heat shrunk in situ about the spline 22 at the end of Step 3, as FIG. 41 shows. As heat is applied, the sleeves 98 shrink about the spline 22, securing the interlaced distal regions 30 individually to the spline elements 22.

Figure 41A:
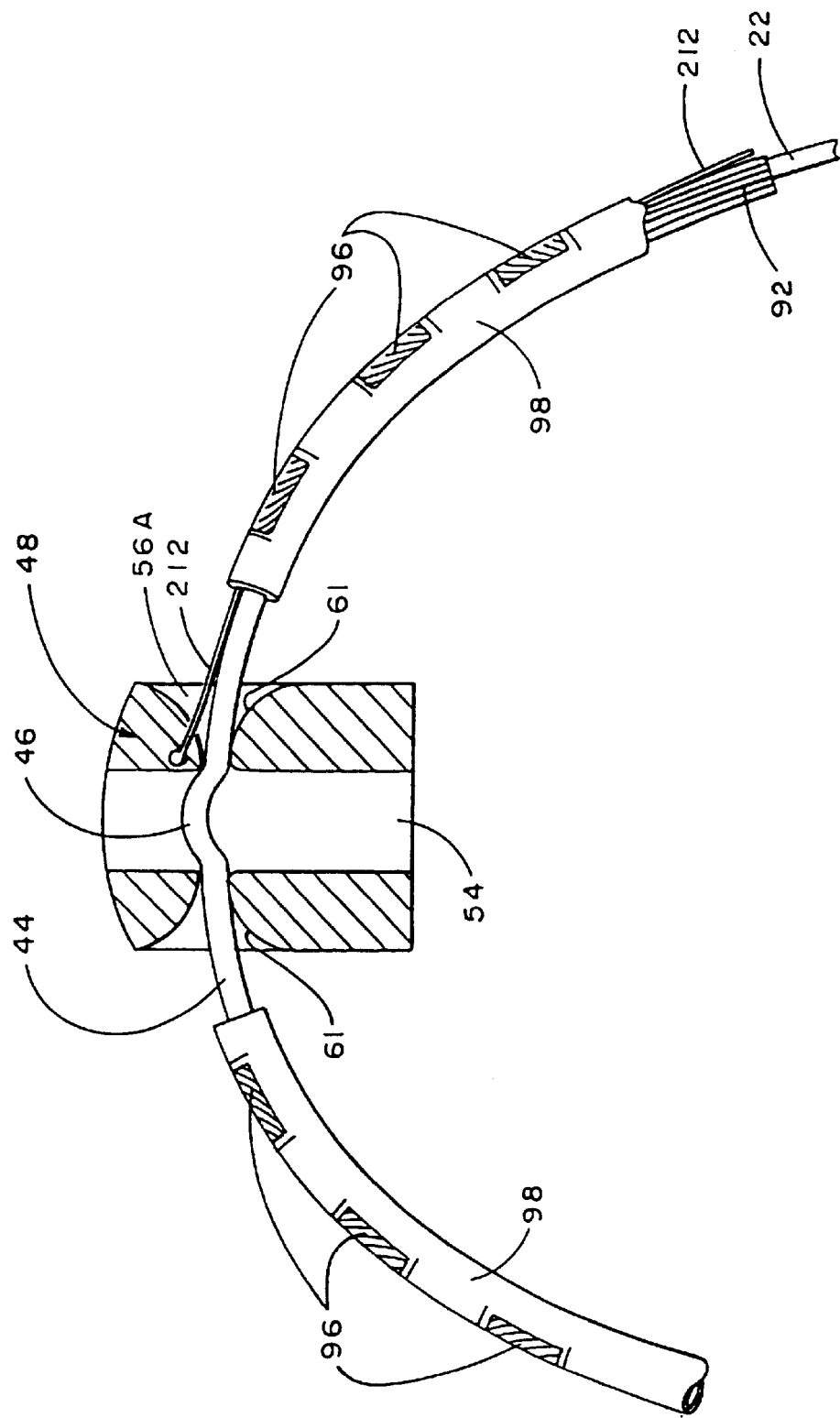
FIG. 41A is an enlarged view of the end cap showing its connection to a signal wire for use as an electrode.

As FIG. 41A shows, an additional insulated signal wire 212 can be passed through one of the sleeves 98 before heat shrinking and electrically connected to the end cap 48. Upon heat shrinking, the sleeve 98 captures the signal wire 212, securing it to the spline element 22. This obtains the benefit of using the end cap 48 as an additional electrode, as previously discussed.

At this time, the free end of the spline elements 22 are fastened to the anchor member 62/lock ring 64 assembly, in the manner previously described. The anchor member 62 is then secured to the distal end 16 of the catheter tube 12 (as FIG. 42 shows).

The intermediate region 34 of the circuit assembly 28(1) comprises the ribbon cables 92 (i.e., C1 and C2) that extend out of each interlaced sleeve 98 (the signal wire 212 leading to the end cap 48 accompanies the ribbon cables 92 associated with the particular spline element 22 along which the wire 212 runs). In the illustrated embodiment, there are eight pairs of ribbon cables 92, two interlaced with each sleeve 98. As FIG. 42 shows, the ribbon cables 92 are helically wrapped in pairs about the exterior of the catheter tube 12 from its distal end 16 to its proximal end 14.

The helical wrapping of the eight pairs of ribbon cables 92 about tube 12 maintains the flexibility of the catheter tube 12. The helical wrapping also minimizes stress on the ribbon cables 92 when the catheter tube 12 is flexed during use.

The helical wrapping of the ribbon cables 92 further presents a low profile, allowing use of a catheter tube 12 having a relatively small diameter. In a representative embodiment, a catheter tube 12 of approximately 0.078 inch in outside diameter will accommodate eight to ten double wrapped pairs of ribbon cables 92 of the type described.

The helical wrapping of the ribbon cables 92 also leaves the interior bore of the catheter tube 12 open. The open interior bore can be used to conduct liquids, or to accommodate another probe for ablation purposes and the like.

Once the intermediate region 34 of the electrode circuit 28(1) is wrapped about the tube 12, an outer sleeve 108 of heat shrink material is slid into place over the wrapped ribbon cable 92 and tube 12 assembly. The application of heat shrinks the outer sleeve 108 into place. As FIG. 42 shows, the sleeve 108 captures the wrapped ribbon cables 92 about the catheter tube 12.

The proximal region 32 of the circuit assembly 28(1) comprises the ribbon cables 92 that extend from the tube 12 into the handle 18 (as FIG. 1A shows). There, the proximal region 32 connects to two commercially available, external high density connectors 36a and 36b.

As FIG. 1A shows, half of the ribbon cables 92 are coupled the connector 36a, while the other half of the ribbon cables 92 are coupled to the connector 36b. In the illustrated embodiment, the connectors 36a and 36b are over-molded about pin assemblies to which the ribbon cables 92 are electrically connected. The connectors 36a and 36b plug into a suitable signal processor (not shown).

FIG. 1B shows an alternative embodiment. In this embodiment, the proximal region 32 connects to a multiplexer 150 carried within the handle 18. All the ribbon cables 32 are electrically coupled to the input of the multiplexer 150. The multiplexer 150 is attached to a single low density connector 152. The multiplexer 150 reduces the number of connection pins the connector 152 carries, so that the connector 152 can be significantly less expensive than the high density connectors 36a and 36b shown in FIG. 1A.

In the embodiment shown in FIG. 1B, the connector 152 plugs into a signal processor 154 which includes a demultiplexer (DMUX) 156 receiving the signals from the multiplexer 150 the probe handle carries. Alternatively, the multiplexed signals can be directly digitized by the signal processor 154 without using a DMUX.

The handle-mounted multiplexer 150 shown in FIG. 1B transfers mostly digital signals. It can therefore can be implemented with relatively straightforward circuitry. It serves as a practical and cost-effective solution to reduce the number of electrical connections in the proximal end of the probe and thereby improve the quality of data acquisition.

FIGS. 55 to 59 show further details of a preferred implementation of mounting the multiplexer 150 in the probe handle 18.

Figure 55:
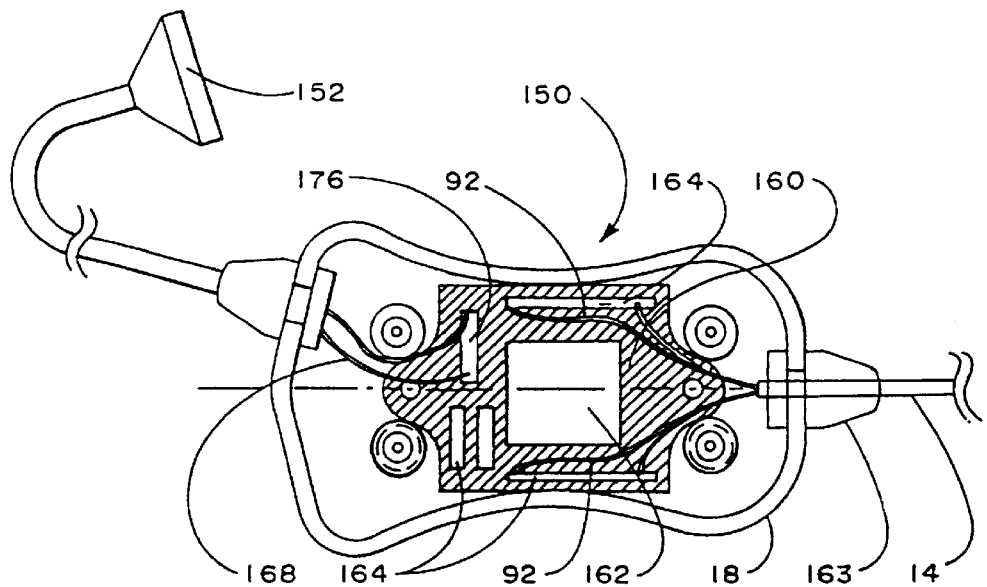
FIG. 55 is a plan view of the interior of the handle shown in FIG. 1B, showing the mounting of a multiplexer therein.

As FIG. 55 shows, the handle 18 carries a printed circuit board (PCB) 160. Screw bosses fix the position of the PCB 160 within the handle 18. The multiplexer 150 comprises a chip 162 surface mounted on the PCB 160. The leads of the chip 162 are connected to the ribbon cables 92 through contact pad arrays 164 (three cables 92 are shown for the purpose of illustration). Preferable a strain relief 163 surrounds the junction of the proximal catheter tube 14 with the handle 18.

Decoupling capacitors 166 are preferable present to prevent malfunction of the chip 162 caused by variations in the supply voltage. Signal lines 168 connected to the output 176 of the chip 162 lead to the low density connector 152.

Figure 56:
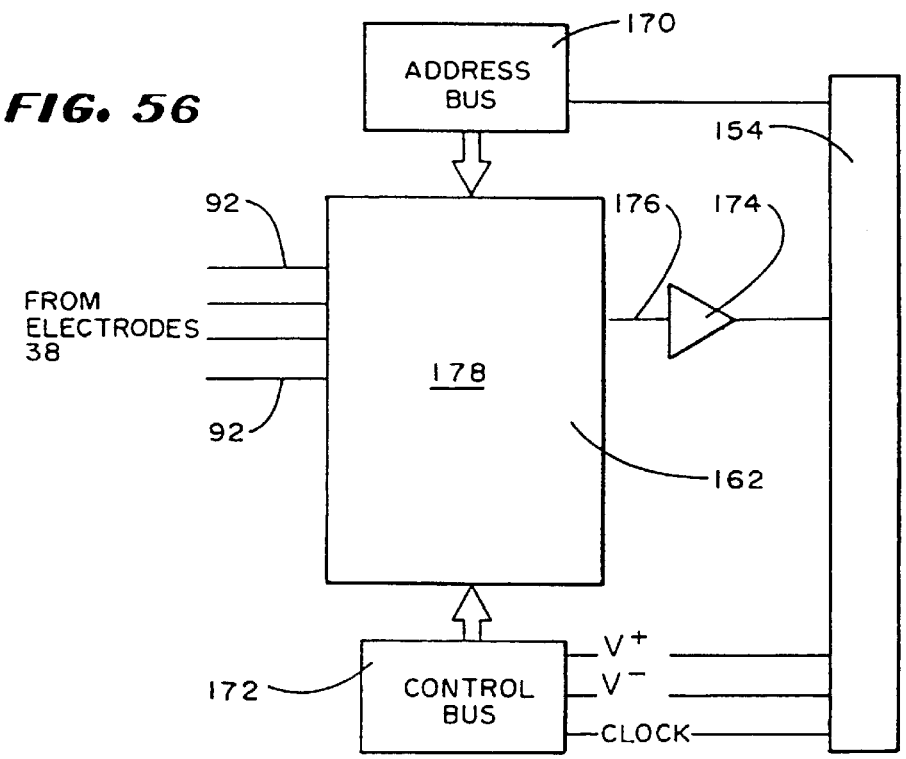
FIG. 56 is a block diagram of the circuitry of the multiplexer carried by the handle shown in FIG. 55.

FIG. 56 is a block diagram of the multiplexer chip 162 itself. The chip 162 includes an address bus 170 and a control bus 172. The address bus 170 has about log2N(e) bits, where N(e) is the number of electrodes 38 carried by the support assembly 20. The address bus 170 and control bus 172 are electrically coupled to the data acquisition components of the signal processor 154. The buses 170 and 172 control data flow through the chip 162 as the processor 154 works to analyze the signals coming from the electrodes 38. The control bus 172 also carries the voltage supply lines V+ and V− and the clock signal from the signal processor 154.

The chip output 176 preferably includes an amplifier 174. The amplifier 174 provides pre-amplification of signals sent to the processor 154 to improve the signal-to-noise ratio. The amplifier 174 can be placed on the same die as the chip 162. Alternatively, the amplifier 174 can be placed on a different die, or it can be a separate component mounted in the probe handle 18.

Figure 57:
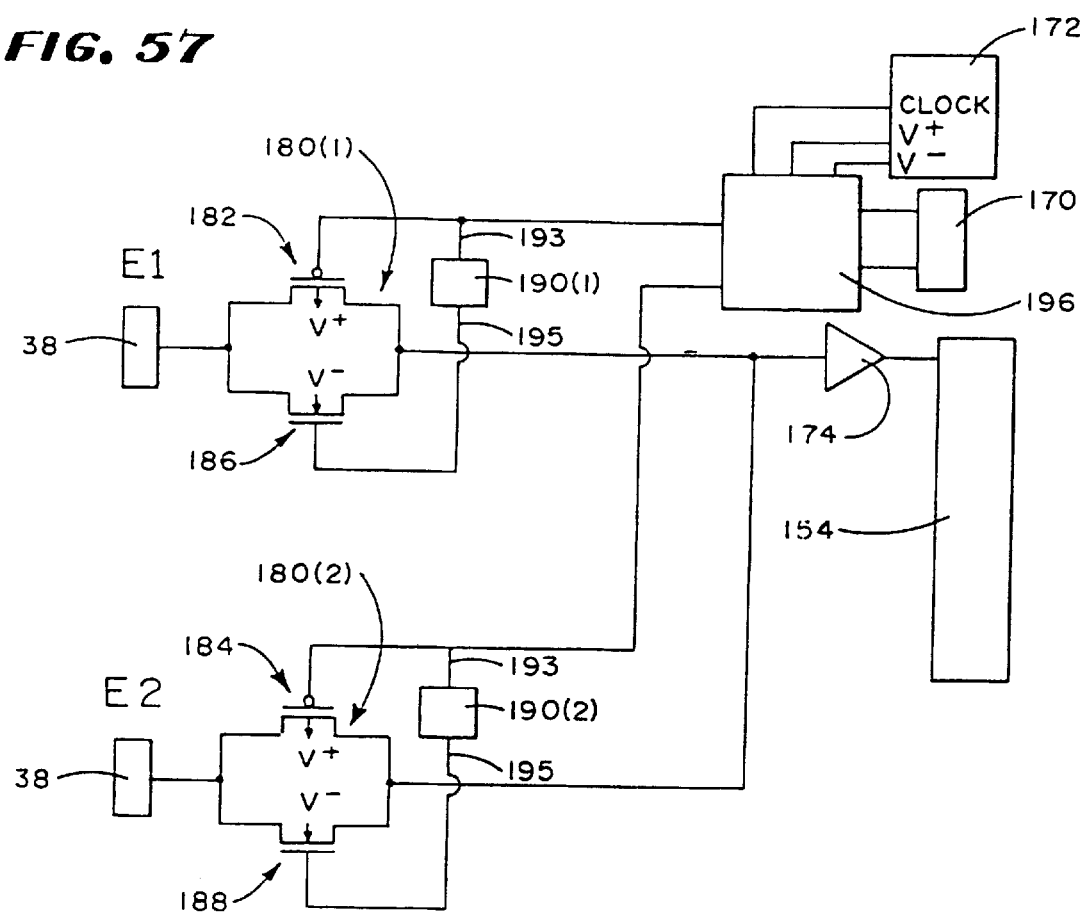
FIG. 57 is a schematic view of the transmission gates associated with the multiplexer shown in block diagram form in FIG. 56.
Figure 58:
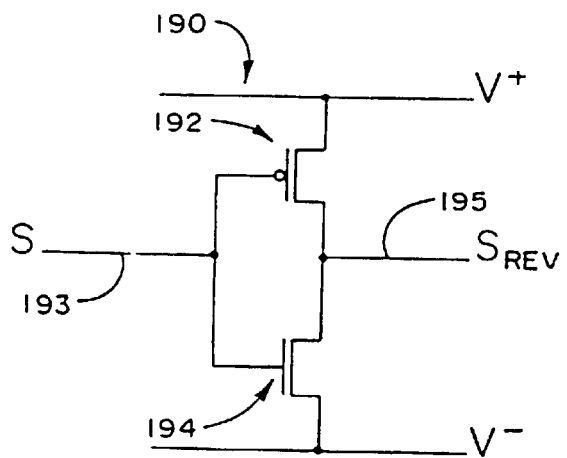
FIG. 58 is a schematic view of an inverter that is associated with the transmission gates shown in FIG. 57.

FIG. 57 shows further details of the multiplexing circuitry 178 of the chip 162, implemented by complimentary metal oxide semiconductor (CMOS) technology. The circuitry 178 includes transmission gates 180, one gate being associated with an electrode 38 carried by the support structure 20 (1). For the sake of illustration, two electrodes E1 and E2 and two gates 180(1) and 180(2) are shown.

The gates 180(1) and 180(2) each are formed by pairs of P-channel MOSFETS 182 and 184 and N-channel MOSFETS 186 and 188. The MOSFETS are metal oxide semiconductor field effect transistors.

Each gate 180(1) and 180(2) is driven by an inverter 190(1) and 190(2). As FIG. 58 further shows, each inverter 190 comprises a P-channel transistor 192 and an N-channel transistor 194 connected in parallel between an input lead 193 and an output lead 195. The transistors 192 and 194 take a given signal (S in FIG. 58) in the input lead 193 and invert it as output ($S_{REV}$) in the output lead 195. In other words, if S is 1, $S_{REV}$ is 0, and vice versa. FIG. 57 also shows the input and output leads 193 and 195 of the inverters 190(1) and 190(2). It should be appreciated that the signals handled by the inverter 190(1) differ from the signals handled by the inverted 190(2), as the respective gates 180(1) and 180(2) serve different electrodes E1 and E2.

As FIG. 57 shows, the inverters 190 are themselves driven by the outputs of an address decoder 196. In the preferred implementation, the decoder 192 comprises a programmable logic array (PLA). The decoder 196 receives input from the voltage supplies and a clock (through the control bus 172) and other input from the address bus 170.

The output of each gate 180(1) and 180(2) is conveyed through the amplifier 174 to the signal processor 154.

Figure 59:
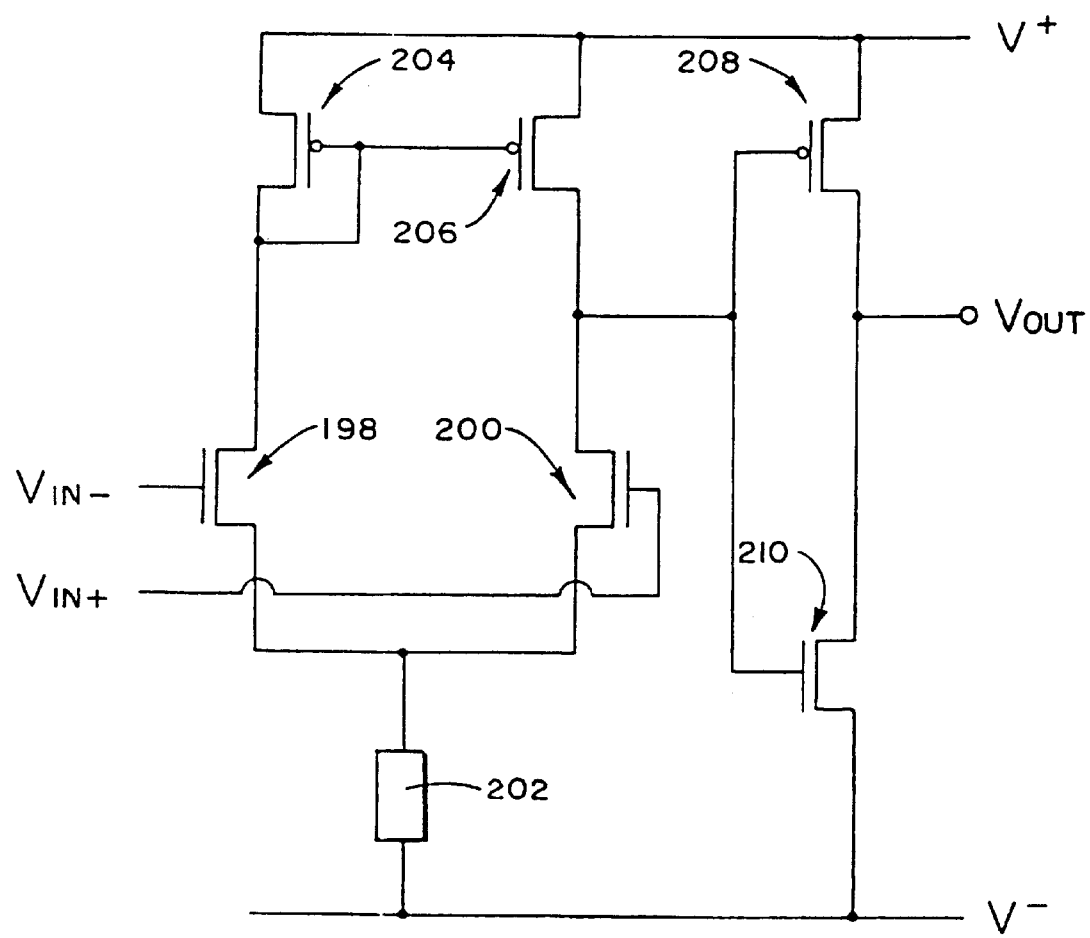
FIG. 59 is a schematic view of the amplifier associated with the multiplexer shown in block diagram form in FIG. 56.

FIG. 59 shows a CMOS implementation of the amplifier 174. N-channel transistors 198 and 200 form a differential input amplifier biased by the current source 202 of the signal processor 154. P-channel transistors 204 and 206 form a current mirror, which acts as an active load for the transistors 198 and 200, thereby increasing the voltage gain. The P-channel transistor 208 and the N-channel transistor 210 form the output stage of the amplifier 174, which is electrically coupled to the signal processor 154.

By mounting the multiplexer 150 in the probe handle 18, the number of electrical connections is considerably reduced. Assuming there are 2N signals coming from the electrodes 34 on the support structure 20, the multiplexer 150 transports N signals from the address bus 170, and 4 additional signals; i.e., the V+; V−; and clock signal from the control bus 172) and the output to the amplifier 174. The multiplexer 150 therefore only requires a total of N+4 pins in the connectors 152.

The handle 18 accommodates in a technically efficient way the mounting the circuitry of the multiplexer 150. It avoids the considerable technical challenges involved in reliably fitting all this circuitry in the very compact regions at the distal end 16 of the tube 12.

(2) Flexible Electrode Circuit

FIGS. 43 to 54 show a preferred embodiment for an electrode circuit assembly, which is identified by reference numeral 28(2) in FIG. 52.

The distal portion 30 of the electrode circuit assembly 28(2) includes a flexible substrate 110 (see FIG. 43). The substrate is a thin sheet of flexible, electrically non-conducting material. KAPTON™ plastic and like materials can serve this purpose.

As FIG. 43 shows, the substrate 110 includes a main body 112 and a tail body 114 that extends at predetermined angle from the main body 112. As will be described in greater detail later, the dog-leg shape of the substrate 110 facilitates the mounting and alignment of the electrode circuit assembly 28(2)on the probe 10.

In the illustrated embodiment, the main substrate body 112 measures about 3 inches in length and about 0.027 inch in width. The tail substrate body 114 measures about 0.6 inch in length and about 0.48 in width. In the illustrated embodiment, the angle between the main body 112 and the tail body 114 (Angle θ in FIG. 43) is about 160°.

As FIGS. 43 and 44 show, the substrate 110 carries an array of spaced apart electrodes pads 116 on the front surface 118 of the main body 112. The electrode pads 116 are preferably deposited upon the front surface 118 by sputtering, vapor deposition, or other appropriate technique.

The illustrated embodiment shows eight, equally spaced electrode pads 116, which are also identified as E1 to E8 in FIG. 43. These pads 116 are spaced apart for uni-polar operation. Of course, more or fewer pads 116 could be applied, and the pads 116 could be grouped into closer spaced pairs for bi-polar operation.

In the illustrated embodiment, each uni-polar electrode pad 116 measures about 0.078 inch. The pads are separated by about 0.164 inch.

Each pad 116 includes a plated through hole or via 120. The via 120 extends through the main substrate body 112 between its front surface 118 and back surface 122 (see FIGS. 43 and 45). In the illustrated embodiment, each via 120 measures about 0.004 inch in diameter.

As FIG. 43 shows, the vias 120 are oriented generally along the centerline of each pad 116, but at progressively increasing distances from the longitudinal edge 124 of the substrate 110. The via 120 for the most distal pad E1 is located closest to the edge 124, while the via 120 for the most proximal pad E8 is located farthest from the edge 124. The intermediate pads E2 to E7 are spaced progressively between these two extremes.

As FIGS. 45 and 46 also show, the substrate 110 also carries an array of connection pads 126 on the back surface 122 of the tail body 114. The number of connection pads 126 equals the number of electrode pads 116. In the illustrated embodiment, there are eight connection pads 126, corresponding to the eight electrode pads 116. The connection pads 126 are also designated CP1 to CP8 in FIGS. 45 and 47.

The connection pads CP1 to CP8, like the electrode pads E1 to E8, are preferably deposited onto the back substrate surface 122 by sputtering, vapor deposition, or other appropriate technique.

Figure 47:
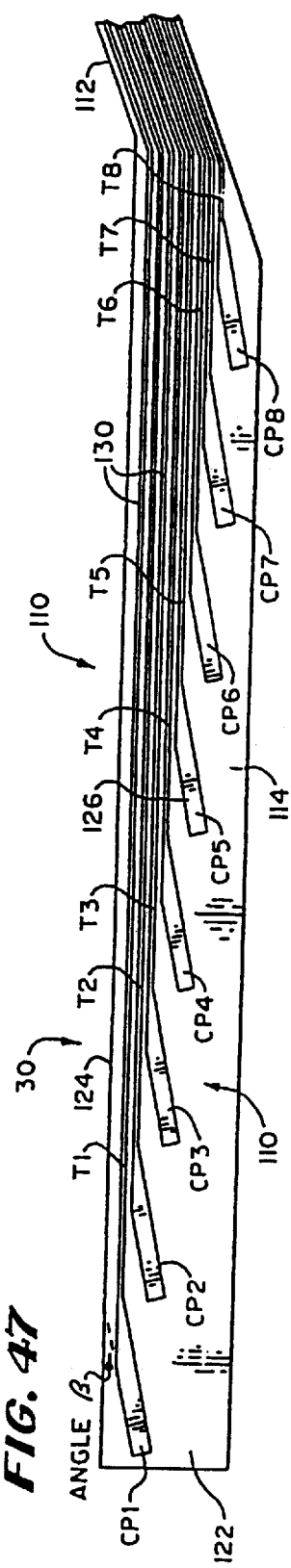
FIG. 47 is an enlarged view of a portion of the back surface of the substrate shown in FIG. 45, showing the details of the connection pads and traces deposited thereon.

As FIG. 47 best shows, the connection pads CP1 to CP8 are applied in a side-by-side, equally spaced array on the back surface 122 of the tail body 114. Like the vias 120, the connection pads CP1 to CP8 are progressively spaced increasing distances from the longitudinal substrate edge 124. The most proximal connection pad (CP1) lies closest to the edge 124, and the most distal connection pad (CP8) lies farthest away from the edge 124. The intermediate pads CP2 to CP7 are spaced progressively between these two extremes.

As FIG. 47 also best shows, the connection pads CP1 to CP8 extend at an angle (Angle β in FIG. 47) from the edge 128. In the illustrated embodiment, the connection pads extend at about a 10° angle from the edge 128 of the tail body 114. The purpose of angling the connection pads will be described in greater detail later.

In the illustrated embodiment, each connection pad 126 measures about 0.010 inch in width and about 0.050 inch in length. They are each spaced apart by about 0.3 inch.

The substrate 110 further carries traces 130 (see FIGS. 45 and 47) that electrically couple one connection pad 126 to one electrode pad 116. The traces are also identified as T1 to T8 in FIG. 47.

The traces T1 to T8 are preferably also deposited by sputtering, vapor deposition, or other appropriate technique upon the back surface 122 of the tail body 114 and main body 112. The traces T1 to T8 extend parallel to the edge 124, with the traces spaced side-by-side at progressively greater distances from the edge 124.

In this arrangement, the trace T1 closest to the edge 124 electrically couples the most proximal connection pad (CP1) to the most distal electrode (E1), through the associated via 120. The next trace T2 electrically couples the second most proximal connection pad (CP2) to the second most distal electrode (E2), through the associated via 120, and so on.

In the illustrated embodiment, each trace 130 is about 0.0017 inch wide. The traces 130 are spaced apart by about 0.002 inch.

The proximal and intermediate regions 32 and 34 of the electrode circuit assembly 28(2)comprises a continuous length of a miniature, multi-conductor ribbon cable 132 (see FIG. 48), like the cable 92 previously described. In the circuit assembly 28(2), the ribbon cable 132 includes parallel tracks of electrical conductive wire equal in number to the number of electrode pads 116. In the illustrated embodiment, the cable 132 has eight tracks. Like the cable 92, conductive wires in the tracks are overlaid with an electrical insulating material 134.

Figure 49:
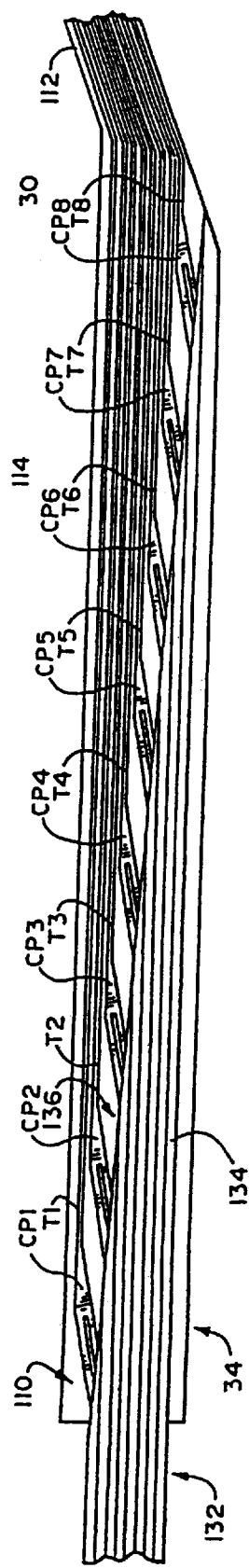
FIG. 49 is a top view showing the ribbon cable shown in FIG. 48 electrically connected to the connection pads shown in FIG. 47.

As FIG. 49 shows, the most distal end 136 of the cable 132 (which forms a part of the intermediate region 34 of the assembly 28(2)) is electrically coupled to the connection pads 126 carried by the substrate 110.

Figure 48:
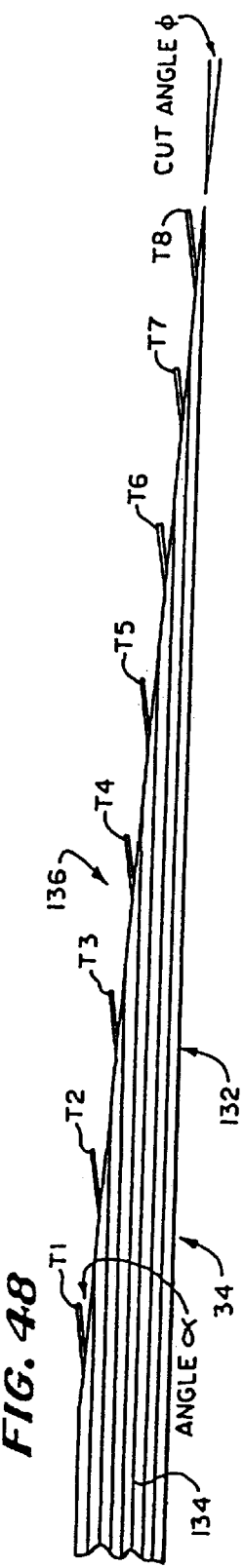
FIG. 48 is a top view of a ribbon cable scarf cut and prepared for electrical connection to the connection pads shown in FIG. 47.

As FIG. 48 shows, before being connected to the connection pads 126, the most distal cable end 136 is scarf cut at a steep acute angle (Angle φ in FIG. 48). The scarf cut end 136 is stripped of insulating material 134 to expose the individual tracks of conductive wire, identified as T1 to T8 in FIGS. 48 and 49.

The individual tracks T1 to T8 are also each bent upward by an angle (Angle α in FIG. 48). Angle α is generally equal to Angle β, the angle at which the connection pads extend from the edge 124 of the substrate 110. Therefore, in the illustrated embodiment, Angle α is about 10°.

The Angles φ, β, and α respectively selected for the scarf cut, the connection pads CP1 to CP8, and the exposed tracks T1 to T8 take into account the physical dimensions of the ribbon cable (i.e., its pitch, width, and thickness), the size constraints physiologically imposed upon the assembly 28(2), and the desired therapeutic performance of the probe 10 dictating the number and arrangement of electrodes. The Angles φ, β, and α are selected, given these multiple considerations, to align the tracks T1 to T8 of the ribbon cable 132 in a technically workable way for resistance welding to the individual connection pads CP1 to CP8.

In the illustrated embodiment, the distance between the wire tracks T1 to T8 on the ribbon cable 132 (i.e., its pitch) is about 0.0039 inch. The eight-track ribbon cable 132 measures about 0.032 inch in width and about 0.004 inch in thickness. The staggered pattern of eight connection pads CP1 to CP8 on the substrate 110 measures about 0.6 inch in horizontal length and about 0.048 inch in vertical width. In this arrangement, scarf cut Angle φ is about 3.5°. This scarf cut, together with a connection pad and connection wire Angles α and β of about 10°, provide a workable alignment, as FIG. 49 shows.

Once the electrical connections between the tracks T1 to T8 of the ribbon cable 132 and substrate 110 is made, the substrate 110 is laced, distal end first (see FIG. 50) through a sleeve 138 containing slits 102 forming eight windows 100 (also numbered W1 to W8) that accommodate the eight electrode pads E1 to E8. The main body 112 of the substrate 110 is laced through the sleeve 138 beginning with the most proximal window W8 toward the most distal window W1 in the same manner that the ribbon cables C1 or C2 are individually laced within the sleeve 98 (as FIGS. 31 to 37 show).

When the main substrate body 112 is laced through the eight windows W1 to W8 of the sleeve 138 (as FIG. 51 shows), the eight electrode pads 116 (E1 to E8) on the substrate 110 project through the eight windows 100 (W1 to W8). The tail body 114 of the substrate 110 and attached ribbon cable 132 extend outward beyond the proximal end of the sleeve 138 (as FIG. 51 also shows).

As FIG. 52 shows, the interlaced sleeve 138 and substrate 110 slides onto the spline elements 22 of the associated support assembly 20(1). The interlaced distal ends 30 are heat shrunk about the spline elements 22, as previously described.

As FIG. 53 shows, the free end of the spline elements 22 (and associated substrate body 112) are fitted into the anchor member 62/lock ring 64 assembly that forms the base 26, in the manner previously described (see FIGS. 10 to 13).

The substrate body 112 preferably includes an alignment mark 140 near its junction with the tail body 114 (see FIGS. 46, 50, and 51). The alignment mark 140 indicates the location where the anchor member 62/lock ring 64 assembly should engage each substrate 110. The mark 140 assures that all substrates 110 and associated spline elements 22 are mutually aligned with each other about the base 26 (see FIG. 53). The mark 140 also assures that the same portion of the main substrate body 112 and the entire tail body 114 extends beyond the base 26, for reasons that will be explained later. The joined base 26 and the support assembly 20(1) is then secured to the distal end 16 of the catheter tube 12 (as FIG. 53 shows).

The intermediate regions 34 of the eight circuit assemblies 28(2) on the support assembly 20(1) (comprising eight ribbon cables 132 attached to the tail bodies 114) are helically wrapped about the exterior of the catheter tube 12 (see FIGS. 53 and 54).

As FIGS. 53 and 54 show, the angled tail body 114 of the substrate 110 directly orients the attached ribbon cable 132 for helical wrapping about the catheter tube 12. In the illustrated embodiment, an Angle θ of 160° presents the ribbon cable 132 for a 20° helical wrap (that is, the angle of the helical wrap and Angle θ of the tail body 114 are supplementary angles).

Given the diameter of the catheter tube 12 (which, in the illustrated embodiment, is about 6 French, or 0.078 inch), a 20° helical wraps overlies the eight ribbon cables 132 in two layers about the tube 12. The ribbon cables 132 for odd numbered spline elements (identified as S1, S3, and S5 in FIGS. 53 and 54) are wrapped on the bottom layer, and the ribbon cables 132 for even numbered spline elements (identified as S2 and S4 are wrapped on the top layer), or vice versa.

Once the ribbon cables 132 are wrapped about the tube 12, the outer sleeve 108 of heat shrink material is slid into place over the tube 12 and wrapped ribbon cables 132, in the manner previously described (see FIG. 42). The application of heat shrinks the outer sleeve 108, capturing the wrapped ribbon cables 132 about the catheter tube 12, as previously described.

With the outer sleeve 108 in place, the catheter tube 12 presents a diameter of about 8 French. And, as before described, the central lumen of the catheter tube 12 is left completely open to accommodate an ablation catheter or the like.

Also as previously described, the proximal regions 32 of the electrode circuits 28(2) are connected within the probe handle 18 to one or more commercially available, external high density connectors 36a and 36b (as FIG. 1A shows) or to a single low density connector 154 via a multiplexer 152 carried in the probe handle 18 (as FIG. 1B shows).

In all embodiments described, the sleeve 98 supports multiple electrodes 38 and adjacent electrical conduction wires associated with the distal region 30 of the electrode circuit assembly 28. The sleeve 98 is itself joined about a stiffener member (i.e., a spline element 22). Multiple sleeve-bearing stiffener members 22 are themselves mechanically connected to and constrained at opposite ends to create the three dimensional support structure 20 for the electrodes 28. The stiffener members 22 orient the electrodes into a predetermined circumferential distribution, while the sleeves retain the electrodes in an exposed, longitudinally separated condition on the stiffener members 22. This structure 20 is supported on a catheter tube 12. The sleeve 98 terminates short of the catheter tube 12, so that the electrical conduction wires of the proximal and intermediate regions 32 and 34 of the electrode circuit assembly 28 are exposed outside the sleeve 98. The intermediate region 34 is stabilized along the catheter tube 12 outside the sleeve 98. The proximal region 32 is enclosed within a handle 18 for attachment to external connectors.

The features of the invention are set forth in the following claims.

We claim:

1. An electrode assembly for a catheter for diagnostic evaluation or therapeutic treatment of endocardial tissue, comprising an electrode circuit having a distal region for carrying at least one electrode, a proximal region for connection to external apparatus, and an intermediate region electrically coupling the distal region with the proximal region, at least one of the distal region, the proximal region, and the intermediate region includes flexible ribbon cable comprising two or more adjacent tracks of electrical conduction material and adjoining electrical insulating material, wherein the distal region comprises a length of the flexible ribbon cable, and further includes a stiffener member supporting the length of flexible ribbon cable, and a hub and a base, wherein the stiffener member is connected to and constrained at opposite ends by the hub and the base to urge the stiffener member into a predetermined curvilinear contour.

2. An assembly according to claim 1 wherein the stiffener member is made from metallic material.

3. An assembly according to claim 1 wherein the stiffener member is made from nickel titanium material.

4. An assembly according to claim 1 wherein the stiffener member is generally rectilinear in cross section.

5. An electrode assembly for a catheter for diagnostic evaluation or therapeutic treatment of endocardial tissue, comprising an electrode circuit having a distal region for carrying at least one electrode, a proximal region for connection to external apparatus, and an intermediate region electrically coupling the distal region with the proximal region, at least one of the distal region, the proximal region, and the intermediate region includes flexible ribbon cable comprising two or more adjacent tracks of electrical conduction material and adjoining electrical insulating material, wherein the distal region includes a flexible substrate that carries an electric circuit including the at least one electrode, wherein the intermediate region includes a length of the flexible ribbon cable electrically coupled to the electrical circuit of the flexible substrate, a stiffener member supporting the flexible substrate, and a hub and a base, wherein the stiffener member is connected to and constrained at opposite ends by the hub and the base to urge the stiffener member into a predetermined curvilinear contour.

6. An assembly according to claim 5 wherein the stiffener member is made from a metallic material.

7. An assembly according to claim 5 wherein the stiffener member is made from a nickel titanium material.

8. An assembly according to claim 5 wherein the stiffener member is generally rectilinear in cross section.

9. An electrode assembly for a catheter for diagnostic evaluation or therapeutic treatment of endocardial tissue, comprising a length of flexible ribbon cable comprising two or more adjacent tracks of electrical conductive wire and adjoining electrical insulating material, a region on at least one of the tracks where the conductive wire is exposed, and an electrode comprising electrical conducting material overlying the region and electrically coupled to the exposed conductive wire.

10. An electrode assembly according to claim 9 wherein the ribbon cable has a width formed by the adjacent tracks and adjoining electrical insulating material, and wherein the electrode extends across the width of the ribbon cable, overlying the region and a contiguous area of the adjacent track.

11. An electrode assembly according to claim 9 wherein the electrode is deposited upon the region.

12. An electrode assembly according to claim 11 wherein the ribbon cable has a width formed by the adjacent tracks and adjoining electrical insulating material, and wherein the electrode is deposited across the width of the ribbon cable, overlying the region and a contiguous area of the adjacent track.

13. An electrode assembly according to claim 11 wherein the electrode comprises an undercoat deposition of titanium and an overcoat deposition of platinum.

14. An electrode assembly according to claim 11 wherein the electrode comprises a deposition of an alloy of platinum and iridium.

15. An electrode assembly according to claim 11 wherein the electrode is about 5 to about 200 microinches thick.

16. An electrode assembly according to claim 9 and further including a stiffener member supporting the length of ribbon cable and the overlying electrode.

17. An electrode assembly according to claim 16 and further including a hub and a base, and wherein the stiffener member is connected to and constrained at opposite ends by the hub and the base to urge the stiffener member into a predetermined curvilinear contour.

18. An assembly according to claim 16 wherein the stiffener member is made from a metallic material.

19. An assembly according to claim 16 wherein the stiffener member is made from a nickel titanium material.

20. An assembly according to claim 16 wherein the stiffener member is generally rectilinear in cross section.

21. An electrode assembly for a catheter for diagnostic evaluation or therapeutic treatment of endocardial tissue, comprising a length of flexible ribbon cable comprising first and second adjacent tracks of electrical conductive wire and adjoining electrical insulating material, a first region on the first track where the conductive wire is exposed, a second region on the second track where the conductive wire is exposed, the first and second regions being longitudinally spaced apart along the length of the ribbon cable by the adjoining electrical insulating material, a first electrode comprising an electrical conducting material overlying the first region and electrically coupled to the exposed conductive wire in the first track, but not to the exposed conductive wire in the second track, and a second electrode comprising an electrical conducting material overlying the second region and electrically coupled to the exposed conductive wire in the second track, but not to the exposed conductive wire in the first track.

22. An electrode assembly according to claim 21 wherein the ribbon cable has a width formed by the adjacent first and second tracks and adjoining electrical insulating material, wherein the first electrode extends across the width of the ribbon cable, overlying the first region and the adjacent second track, and wherein the second electrode extends across the width of the ribbon cable, overlying the second region and a contiguous area of the adjacent first track.

23. An electrode assembly according to claim 21 wherein the electrode is deposited upon the region.

24. An electrode assembly according to claim 22 wherein the ribbon cable has a width formed by the adjacent tracks and adjoining electrical insulating material, wherein the first electrode is deposited across the width of the ribbon cable, overlying the first region and a contiguous area of the adjacent second track, and wherein the second electrode is deposited across the width of the ribbon cable, overlying the second region and a contiguous area of the adjacent first track.

25. An electrode assembly according to claim 23 wherein the first and second electrodes each comprise an undercoat deposition of titanium and an overcoat deposition of platinum.

26. An electrode assembly according to claim 23 wherein the first and second electrodes each comprise a deposition of an alloy of platinum and iridium.

27. An electrode assembly according to claim 23 wherein the first and second electrodes are each about 5 to 200 microinches thick.

28. An electrode assembly according to claim 21 and further including a stiffener member supporting the length of ribbon cable and the overlying first and second electrodes.

29. An electrode assembly according to claim 28 and further including a hub and a base, and wherein the stiffener member is connected to and constrained at opposite ends by the hub and the base to urge the stiffener member into a predetermined curvilinear contour.

30. An assembly according to claim 28 wherein the stiffener member is made from a metallic material.

31. An assembly according to claim 28 wherein the stiffener member is made from a nickle titanium material.

32. An assembly according to claim 28 wherein the stiffener member is generally rectilinear in cross section.

33. A catheter comprising
a guide body having a distal end, and
an electrode assembly according to claim 9 or 21 supported at the distal end.

34. A catheter according to claim 33 and further including a stiffener member supporting the electrode assembly beyond the distal end of the guide body.

35. A catheter according to claim 34 and further including a base carried by the distal end of the catheter body and a hub, wherein the stiffener member includes proximal and distal ends attached to constrained by, respectively, the base and the hub to urge the stiffener member into a predetermined curvilinear contour.

36. A catheter according to claim 34 wherein the stiffener member is made from a metallic material.

37. A catheter according to claim 34 wherein the stiffener member is made from a nickle titanium material.

38. A catheter according to claim 34 wherein the stiffener member is generally rectilinear in cross section.

39. A catheter for diagnostic evaluation or therapeutic treatment of endocardial tissue, comprising
a guide body having a proximal end and a distal end,
a handle attached to the proximal end of the guide body,
an electrode assembly comprising
a distal region carrying at least one electrode attached to the distal end of the guide body,
an intermediate region extending from the distal region and carried by the guide body between its distal and proximal ends, and
a proximal region extending from the intermediate region and carried by the handle, wherein at least one of the distal region, the proximal region, and the intermediate region of the electrode assembly comprises a length of flexible ribbon cable, the ribbon cable comprising two or more adjacent tracks of electrical conduction material and adjoining electrical insulating material, and
a multiplexer carried by the handle, the multiplexer including an input electrically coupled to the proximal region of the electrode assembly in the handle and an output electrically coupled to a connector member outside the handle.

40. A catheter according to claim 39 wherein the distal region, the proximal region, and the intermediate region of the electrode assembly includes a continuous length of flexible ribbon cable comprising two or more adjacent tracks of electrical conduction material and adjoining electrical insulating material.

41. A catheter according to claim 39 and further including a stiffener member supporting the length of flexible ribbon cable that comprises the distal end of the electrode assembly.

42. A catheter according to claim 41 and further including a hub and a base, and wherein the stiffener member is connected to and constrained at opposite ends by the hub and the base to urge the stiffener member into a predetermined curvilinear contour.

43. A catheter according to claim 41 wherein the stiffener member is made from a metallic material.

44. A catheter according to claim 41 wherein the stiffener member is made from a nickle titanium material.

45. A catheter according to claim 41 wherein the stiffener member is generally rectilinear in cross section.

46. A catheter according to claim 39 wherein the distal region includes a flexible substrate that carries an electric circuit including the at least one electrode, and
wherein the intermediate and proximal regions include a continuous length of the flexible ribbon cable electrically coupled at one end to the electrical circuit of the flexible substrate and to the other end to the multiplexer.

47. A catheter according to claim 46 and further including a stiffener member supporting the flexible substrate.

48. A catheter according to claim 47 and further including a hub and a base, and wherein the stiffener member is connected to and constrained at opposite ends by the hub and the base to urge the stiffener member into a predetermined curvilinear contour.

49. A catheter according to claim 47 wherein the stiffener member is made from a metallic material.

50. A catheter according to claim 47 wherein the stiffener member is made from a nickle titanium material.

51. A catheter according to claim 47 wherein the stiffener member is generally rectilinear in cross section.

* * * * *